(12) United States Patent
Kubota et al.

(10) Patent No.: US 9,917,245 B2
(45) Date of Patent: Mar. 13, 2018

(54) PIEZOELECTRIC ELEMENT, METHOD OF MANUFACTURING PIEZOELECTRIC ELEMENT, PIEZOELECTRIC ACTUATOR, AND ELECTRONIC APPARATUS

(71) Applicant: CANON KABUSHIKI KAISHA, Tokyo (JP)

(72) Inventors: Makoto Kubota, Yokohama (JP); Takanori Matsuda, Chofu (JP); Kaoru Miura, Matsudo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 15/354,349

(22) Filed: Nov. 17, 2016

(65) Prior Publication Data
US 2017/0155037 A1 Jun. 1, 2017

(30) Foreign Application Priority Data
Nov. 27, 2015 (JP) .................................. 2015-231845

(51) Int. Cl.
*B41J 2/045* (2006.01)
*H01L 41/187* (2006.01)
(Continued)

(52) U.S. Cl.
CPC ............ *H01L 41/1871* (2013.01); *A61B 8/00* (2013.01); *B06B 1/06* (2013.01); *B41J 2/14233* (2013.01);
(Continued)

(58) Field of Classification Search
CPC .............. H01L 41/1878; H01L 41/187; H01L 41/1871; H01L 21/31691; H01L 41/1876;
(Continued)

(56) References Cited

U.S. PATENT DOCUMENTS 7,033,521 B2   4/2006   Iwashita et al.
8,529,785 B2   9/2013   Kubota et al.
(Continued)

FOREIGN PATENT DOCUMENTS

JP   2004-006722 A   1/2004
JP   2011-243722 A   12/2011

OTHER PUBLICATIONS

U.S. Appl. No. 15/354,297, filed Nov. 17, 2016, Matsuda et al.
(Continued)

*Primary Examiner* — An Do
(74) *Attorney, Agent, or Firm* — Fitzpatrick, Cella, Harper & Scinto

(57) ABSTRACT

Provided is a piezoelectric element including a substrate, electrodes, and a piezoelectric film, the piezoelectric film including an oxide including Ba, Ca, Ti, and Zr, and at least one element of Mn and Bi in which: $0.09 \leq x \leq 0.30$ is satisfied, where x is a mole ratio of Ca to a sum of Ba and Ca; $0.025 \leq y \leq 0.085$ is satisfied, where y is a mole ratio of Zr to a sum of Ti, Zr, and Sn; and $0 \leq z \leq 0.02$ is satisfied, where z is a mole ratio of Sn to the sum of Ti, Zr, and Sn; a total content $S_{ave}$ of Mn and Bi is 0.0020 moles or more and 0.0150 moles or less for 1 mole of the oxide; and a total content $S_{bou}$ of Mn and Bi in a region of the piezoelectric film adjacent to one of the electrodes is smaller than $S_{ave}$.

33 Claims, 10 Drawing Sheets

(51) Int. Cl.
*B06B 1/06* (2006.01)
*B41J 2/14* (2006.01)
*H01L 41/047* (2006.01)
*H01L 41/08* (2006.01)
*H01L 41/09* (2006.01)
*H01L 41/27* (2013.01)
*H01L 41/297* (2013.01)
*H02N 2/18* (2006.01)
*H03H 9/64* (2006.01)
*A61B 8/00* (2006.01)
*G01C 19/56* (2012.01)
*G02B 26/04* (2006.01)
*H01L 41/318* (2013.01)

(52) U.S. Cl.
CPC ............. *G01C 19/56* (2013.01); *G02B 26/04* (2013.01); *H01L 41/047* (2013.01); *H01L 41/0471* (2013.01); *H01L 41/0815* (2013.01); *H01L 41/09* (2013.01); *H01L 41/0973* (2013.01); *H01L 41/0986* (2013.01); *H01L 41/27* (2013.01); *H01L 41/297* (2013.01); *H01L 41/318* (2013.01); *H02N 2/186* (2013.01); *H03H 9/64* (2013.01)

(58) Field of Classification Search
CPC .... B41J 2/14233; B41J 2/161; B41J 2/14274; B41J 2/1612; B41J 2202/03

USPC ............................... 347/68, 70–72; 29/25.35
See application file for complete search history.

(56) References Cited

U.S. PATENT DOCUMENTS

| | | | |
|---|---|---|---|
| 8,547,001 | B2 | 10/2013 | Saito et al. |
| 8,980,117 | B2 | 3/2015 | Kubota et al. |
| 9,022,531 | B2 | 5/2015 | Kubota et al. |
| 9,022,534 | B2 | 5/2015 | Yabuta et al. |
| 9,082,975 | B2 | 7/2015 | Kubota et al. |
| 9,082,976 | B2 | 7/2015 | Kubota et al. |
| 9,231,188 | B2 | 1/2016 | Suzuki et al. |
| 9,252,685 | B2 | 2/2016 | Ifuku et al. |
| 9,306,149 | B2 | 4/2016 | Hayashi et al. |
| 2016/0104833 | A1 | 4/2016 | Suzuki et al. |
| 2016/0204336 | A1 | 7/2016 | Shimizu et al. |

OTHER PUBLICATIONS

U.S. Appl. No. 15/354,319, filed Nov. 17, 2016, Kubota et al.
U.S. Appl. No. 15/354,277, filed Nov. 17, 2016, Matsuda et al.
Saburo Nagakura et al. (ed.), Iwanami Physicochemical Dictionary, Fifth Edition, pp. 1-3 (Iwanami Shoten, Publishers; Feb. 1998) (English language translation).
Non-Final Office Action in U.S. Appl. No. 15/354,319 (dated Jul. 7, 2017).

PIEZOELECTRIC ELEMENT, METHOD OF MANUFACTURING PIEZOELECTRIC ELEMENT, PIEZOELECTRIC ACTUATOR, AND ELECTRONIC APPARATUS

BACKGROUND OF THE INVENTION

Field of the Invention

The present invention relates to a thin film type piezoelectric element substantially containing no lead therein, and a method of manufacturing the piezoelectric element. The present invention also relates to a piezoelectric actuator, a liquid ejection head, a liquid ejection apparatus, a vibration correction mechanism, a variable optical member, a movable optical member, an optical device, an image pickup apparatus, an optical switch, a micromirror device, an ultrasonic wave probe, an ultrasonograph, a sound component, an angular velocity sensor, a vibration power generator, a surface acoustic wave generator, a piezoelectric shutter, and an electronic apparatus using the piezoelectric element.

Description of the Related Art

A thin film type piezoelectric element typically includes a lower electrode, an upper electrode, and a piezoelectric film sandwiched therebetween. The piezoelectric film is formed of a polycrystal of a ferroelectric metal oxide. A typical principal component of the piezoelectric film is an $ABO_3$ type perovskite-type metal oxide, e.g., lead zirconate titanate (hereinafter referred to as "PZT"). However, PZT contains lead as an A-site element, and thus, influence thereof on the environment is perceived as a problem. Therefore, a piezoelectric film containing no lead therein (lead-free piezoelectric film) is required.

As a lead-free piezoelectric film, a barium titanate film and a calcium barium zirconate titanate film as a partial substitution product thereof are known. In Japanese Patent Application Laid-Open No. 2004-006722, there is disclosed a (Ba, Ca, Sr) (Ti, Zr, Hf)$O_3$ piezoelectric film that is oriented in a specific crystal orientation and is excellent in initial piezoelectric properties.

However, the oriented piezoelectric film is manufactured based on crystal lattice consistency between the piezoelectric film and a buffer layer thereunder, and thus, stress due to lattice misfit or difference in thermal expansion coefficient is produced in the film. Further, in the piezoelectric film, it is difficult to precisely control a composition ratio between an alkaline-earth metal at an A-site and a transition metal at a B-site, and thus, a number of site deficits (oxygen deficits and the like) exist in the film. Because of such internal stress and site deficits, when an oriented piezoelectric film as in Japanese Patent Application Laid-Open No. 2004-006722 is continuously driven, there are problems such as lowered piezoelectric properties (piezoelectric constant and the like), separation between the piezoelectric film and a substrate, and a crack developed in the piezoelectric film.

In order to deal with such problems, there is a technology of suppressing a crack by adding a manganese oxide of 2 mol % or more and 4 mol % or less to a nonepitaxial oriented barium zirconate titanate film as in, for example, Japanese Patent Application Laid-Open No. 2011-243722. The manganese component is expected to have the effect of compensating for site deficits in the piezoelectric film.

However, in a piezoelectric film having a composition as in Japanese Patent Application Laid-Open No. 2011-243722, there is another problem in that the added manganese component moves through the piezoelectric film while the piezoelectric element is manufactured or driven to react with a metal forming an electrode. As a result, the piezoelectric properties are lowered while the piezoelectric element is continuously driven.

SUMMARY OF THE INVENTION

The present invention has been made to solve the problems described above, and provides a thin film piezoelectric element having a piezoelectric constant that does not change much while the piezoelectric element is continuously driven, and a manufacturing method therefor.

The present invention also provides a piezoelectric actuator, a liquid ejection head, a liquid ejection apparatus, a vibration correction mechanism, a variable optical member, a movable optical member, an optical device, an image pickup apparatus, an optical switch, a micromirror device, an ultrasonic wave probe, an ultrasonograph, a sound component, an angular velocity sensor, a vibration power generator, a surface acoustic wave generator, a piezoelectric shutter, and an electronic apparatus using the piezoelectric element.

According to one embodiment of the present invention, there is provided a piezoelectric element, including, on a substrate: a piezoelectric film; and a plurality of electrodes sandwiching the piezoelectric film, or, including: a substrate; a piezoelectric film; and a plurality of comb electrodes laminated in this order.

The piezoelectric film contains a principal component including a perovskite-type metal oxide expressed by the following general formula (1), and an auxiliary component including at least one of Mn and Bi. A total content $S_{ave}$ of Mn and Bi in the composition of the entire piezoelectric film is 0.0020 moles or more and 0.0150 moles or less for 1 mole of the metal oxide, and a total content $S_{bou}$ of Mn and Bi in a region of the piezoelectric film adjacent to one electrode is smaller than $S_{ave}$:

$$(Ba_{1-x}Ca_x)(Ti_{1-y-z}Zr_ySn_z)O_3 \qquad (1)$$

provided that $0.09 \leq x \leq 0.30$, $0.025 \leq y \leq 0.085$, and $0 \leq z \leq 0.02$.

According to one embodiment of the present invention, there is provided a method of manufacturing a piezoelectric element, including:

(a) applying a first raw material liquid onto a substrate having a first electrode layer formed on a surface thereof to form an applied layer;

(b) firing the applied layer every time the applied layer is formed to form a piezoelectric body layer, the steps (a) and (b) being conducted once or a plurality of times to form a piezoelectric film lower layer;

(c) applying a second raw material liquid onto the piezoelectric film lower layer to form an applied layer;

(d) firing the applied layer every time the applied layer is formed to form a piezoelectric body layer, the steps (c) and (d) being conducted once or a plurality of times to form a piezoelectric film intermediate layer;

(e) applying a third raw material liquid onto the piezoelectric film intermediate layer to form an applied layer;

(f) firing the applied layer every time the applied layer is formed to form a piezoelectric body layer, the steps (e) and (f) being conducted once or a plurality of times to form a piezoelectric film upper layer; and (g) forming a second electrode layer on a surface of the piezoelectric film upper layer to manufacture the piezoelectric element, in which the second raw material liquid includes Ba, Ca, Ti, and Zr, and includes at least one of Mn and Bi, and in which the first raw material liquid and the third raw material liquid include Ba, Ca, Ti, and Zr, with a concentration of a sum of Mn and Bi in the first raw material liquid and the third raw material liquid being 1,000 ppm or less.

According to one embodiment of the present invention, there is provided a piezoelectric actuator, including: the above-mentioned piezoelectric element; and a diaphragm provided in contact with the piezoelectric element.

According to one embodiment of the present invention, there is provided a liquid ejection head, including: an ejection orifice; a liquid chamber communicating with the ejection orifice; a diaphragm corresponding to the liquid chamber; and the piezoelectric element corresponding to the diaphragm. Using change in volume in the liquid chamber caused by the piezoelectric element, liquid in the liquid chamber is ejected through the ejection orifice.

According to one embodiment of the present invention, there is provided a liquid ejection apparatus, including: a placing portion for a transfer target; and the above-mentioned liquid ejection head.

According to one embodiment of the present invention, there is provided a vibration correction mechanism configured to reduce the influence of a vibration from the outside while a transfer target is conveyed, and including two or more piezoelectric actuators described above, in which the two or more piezoelectric actuators are arranged such that, when a voltage is applied thereto, the two or more piezoelectric actuators expand and contract in two or more directions.

According to one embodiment of the present invention, there is provided a variable optical member including: at least the above-mentioned piezoelectric actuator and an optical member dynamically connected to the piezoelectric actuator; and a mechanism for changing a shape of the optical member through deformation of the piezoelectric actuator.

According to one embodiment of the present invention, there is provided a movable optical member including: at least the above-mentioned piezoelectric actuator and an optical member dynamically connected to the piezoelectric actuator; and a mechanism for moving and/or rotating the optical member through deformation of the piezoelectric actuator.

According to one embodiment of the present invention, there is provided an optical device including: the vibration correction mechanism described above; and an optical member as a transfer target thereof, or, including the variable optical member described above or the movable optical member described above.

According to one embodiment of the present invention, there is provided an image pickup apparatus including: the vibration correction mechanism described above; and an image pickup element unit as a transfer target thereof.

According to one embodiment of the present invention, there is provided an optical switch including the above-mentioned variable optical member or the above-mentioned movable optical member.

According to one embodiment of the present invention, there is provided a micromirror device including at least: a plurality of micromirrors; and a plurality of the above-mentioned piezoelectric actuators dynamically connected to the plurality of micromirrors, respectively.

According to one embodiment of the present invention, there is provided an ultrasonic wave probe for observing the inside of a subject, the ultrasonic wave probe including the piezoelectric actuator described above, and having a function of oscillating an ultrasonic wave and a function of receiving a reflected wave.

According to one embodiment of the present invention, there is provided an ultrasonograph including: the above-mentioned ultrasonic wave probe; a signal processing unit; and an image generating unit.

According to one embodiment of the present invention, there is provided a sound component including the above-mentioned piezoelectric actuator and having a function of one of sending and receiving sound through driving of the piezoelectric actuator.

According to one embodiment of the present invention, there is provided an angular velocity sensor including the above-mentioned piezoelectric element and having a function of converting change in shape of the piezoelectric element into angular velocity information.

According to one embodiment of the present invention, there is provided a vibration power generator, including the above-mentioned piezoelectric element and having a power generation function of converting vibrational energy into electric energy.

According to one embodiment of the present invention, there is provided a surface acoustic wave generator including the above-mentioned piezoelectric element.

According to one embodiment of the present invention, there is provided a piezoelectric shutter including at least the above-mentioned surface acoustic wave generator and a light-shielding component, the piezoelectric shutter having a function of moving the light-shielding component through driving of the surface acoustic wave generator.

Further features of the present invention will become apparent from the following description of exemplary embodiments with reference to the attached drawings.

DESCRIPTION OF THE EMBODIMENTS

Now, exemplary embodiments of the present invention are described.

According to the present invention, there is provided a piezoelectric element, including:
a substrate;
electrodes; and
a piezoelectric film,
in which the piezoelectric film includes an oxide including Ba, Ca, Ti, and Zr, and at least one element of Mn and Bi,
in which 0.09≤x≤0.30 is satisfied,
where x is a mole ratio of Ca to a sum of Ba and Ca,
in which 0.025≤y≤0.085 is satisfied,
where y is a mole ratio of Zr to a sum of Ti, Zr, and Sn,
in which 0≤z≤0.02 is satisfied,
where z is a mole ratio of Sn to the sum of Ti, Zr, and Sn,
in which a total content $S_{ave}$ of Mn and Bi is 0.0020 moles or more and 0.0150 moles or less for 1 mole of the oxide, and
in which a total content $S_{bou}$ of Mn and Bi in a region of the piezoelectric film adjacent to one of the electrodes is smaller than $S_{ave}$.

More specifically, the piezoelectric film includes a perovskite-type metal oxide expressed by the following general formula (1):

$(Ba_{1-x}Ca_x)(Ti_{1-y-z}Zr_ySn_z)O_3$     (1)

provided that 0.09≤x≤0.30, 0.025≤y≤0.085, and 0≤z≤0.02.

(Configuration of Piezoelectric Element)

Figure 1A:
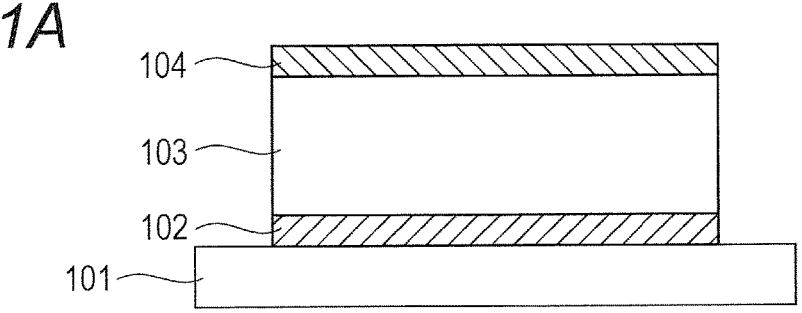
FIG. 1A, FIG. 1B, and FIG. 1C are schematic sectional views for illustrating configurations of a piezoelectric element according to an embodiment of the present invention.
Figure 1B:
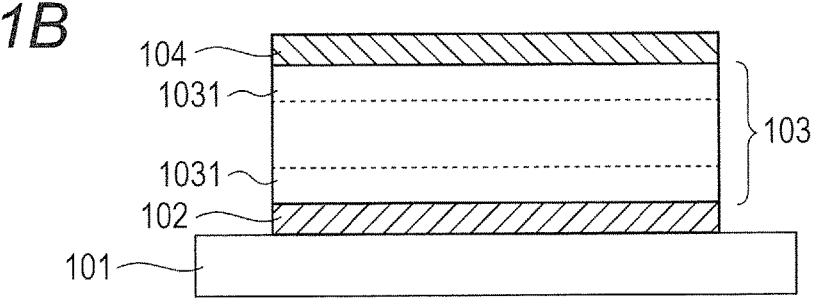
Figure 1C:
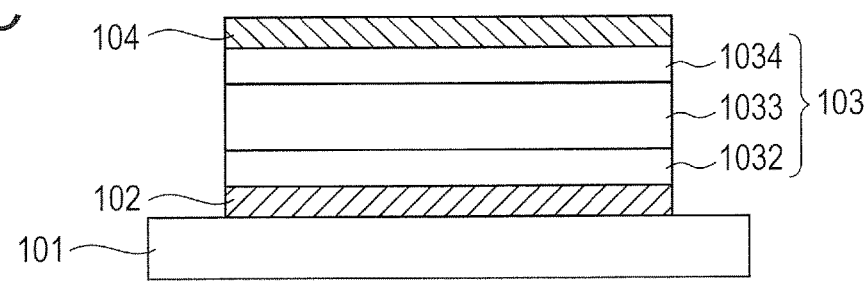

A piezoelectric element according to a first embodiment of the present invention includes, on a substrate, a piezoelectric film and a plurality of electrodes formed so as to sandwich the piezoelectric film. FIG. 1A to FIG. 1C are schematic sectional views for illustrating an exemplary piezoelectric element according to the embodiment. The plurality of electrodes may be a pair of electrodes sandwiching the piezoelectric film, may be patterned electrodes, or may have a configuration in which an electrode for another purpose is formed on a side surface of the piezoelectric film.

With reference to FIG. 1A to FIG. 1C, a configuration in which a substrate 101, a first electrode 102, a piezoelectric film 103, and a second electrode 104 are laminated in this order is described. Note that, like reference numerals are hereinafter used to designate like members.

FIG. 1A is an illustration of an embodiment in which the first electrode 102, the piezoelectric film 103, and the second electrode 104 have the same area and end portions thereof are aligned in a direction perpendicular to the substrate 101, but the mode of the piezoelectric element of the present invention is not limited to that illustrated in FIG. 1A. Areas and shapes of the substrate, the electrodes, and the piezoelectric film can be freely changed depending on a use of the piezoelectric element. Further, insofar as the function of the piezoelectric element is not impaired, other members may be formed between the members. For example, an adhering component for enhancing adherence between the members or a buffer component for enhancing crystallinity may be formed.

Figure 15A:
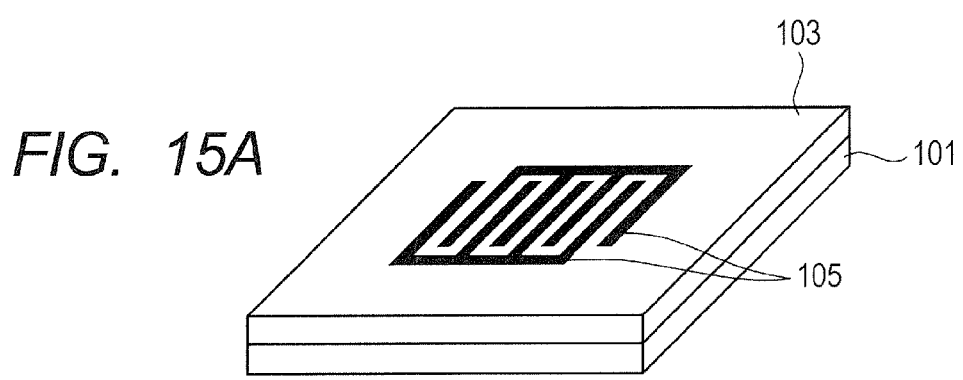
FIG. 15A, FIG. 15B, FIG. 15C, and FIG. 15D are schematic views for illustrating a configuration of a surface acoustic wave generator according to an embodiment of the present invention and for illustrating a configuration of a piezoelectric shutter according to an embodiment of the present invention.

A piezoelectric element according to a second embodiment of the present invention has at least a configuration in which a substrate 101, a piezoelectric film 103, and a plurality of comb electrodes 105 are laminated in this order. FIG. 15A is a schematic perspective view for illustrating an exemplary piezoelectric element according to the embodiment. The number of the comb electrodes 105 is two or more and is not limited to the ones illustrated in FIG. 15A, but it is preferred that two comb electrodes form a pair and comb portions thereof be engaged with each other. It is preferred that the number of the comb electrodes 105 be a multiple of two. The substrate 101 and the piezoelectric film 103 may be patterned.

(Substrate)

A material of the substrate 101 is not limited, but a material that does not deform and melt in a heating step when the first electrode 102, the piezoelectric film 103, and the second electrode 104 are formed is preferred. A maximum temperature in the heating step is typically 800° C. or lower. For example, it is preferred to use a monocrystalline substrate of magnesium oxide (MgO), strontium titanate ($SrTiO_3$), lanthanum aluminate ($LaAlO_3$), or the like, a ceramic substrate of zirconia ($ZrO_2$), alumina ($Al_2O_3$), silica ($SiO_2$), or the like, a semiconductor substrate of silicon (Si), tungsten (W), or the like, or a heat-resistat stainless steel (SUS) substrate. A plurality of kinds of those materials may be combined, or may be laminated to be used as a multilayer configuration.

When the piezoelectric film 103 is selectively oriented in a direction perpendicular to a surface of the substrate 101, it is preferred that underlayers such as the substrate 101 and the first electrode 102 be similarly oriented. In that case, it is preferred to use a monocrystalline substrate as the substrate 101.

(Electrode)

The piezoelectric element according to the present invention includes the electrodes, and thus, a voltage can be applied to the piezoelectric film 103 to cause a piezoelectric strain or to take out an electrical signal corresponding to a strain on the piezoelectric film 103. A material of the electrodes is not particularly limited, and may be one that is ordinarily used for a piezoelectric element. For example, a metal such as Ti, Pt, Ta, Ir, Sr, In, Sn, Au, Al, Fe, Cr, Ni, Pd, Ag, Cu, or Ru and a compound thereof may be used.

It is preferred that, from the viewpoint of having excellent conductivity, the electrodes included in the piezoelectric element according to the present invention be metal electrodes. In particular, from the viewpoint of conductivity and durability, it is preferred that the electrodes be metal electrodes containing any one of Au, Ag, Pd, Pt, Ni, and Ru. It is preferred that a metal component other than Au, Ag, Pd, Pt, Ni, and Ru that is contained in the electrodes be at 1,000 ppm or less, and it is more preferred that the metal component be at 500 ppm or less. In particular, it is preferred that a sum of Mn and Bi be at less than 50 ppm. It is herein determined that, if "the sum of Mn and Bi is smaller than 50 ppm", then "Mn and Bi are not contained". When the sum of Mn and Bi contained in the electrodes is at less than 50 ppm, the possibility that an extent of reduction of a piezoelectric constant while the piezoelectric element is continuously driven increases can be reduced, which is more preferred.

A preferred thickness of the electrodes is 50 nm or more and 500 nm or less.

A plurality of the electrodes, for example, the first electrode 102 and the second electrode 104, may be formed of materials different from each other.

Methods of manufacturing the first electrode 102, the second electrode 104, and the comb electrodes 105 are not limited, but a high-density electrode thin film having an excellent conductivity can be obtained through use of a method selected from sputtering, vapor deposition, and chemical solution deposition (CSD). A particularly desired manufacturing method is DC sputtering. Further, the electrodes may be patterned in a desired shape.

Electrode widths and electrode pitches of the comb electrodes 105 are not particularly limited, and are selected depending on properties of an excited surface acoustic wave, but, for example, electrode widths and electrode pitches of 10 μm or more and 500 μm or less are appropriate for excitation of a surface acoustic wave.

(Piezoelectric Film)

The piezoelectric film of the present invention refers to a thin film-like crystalline aggregate exhibiting a positive piezoelectric effect or an inverse piezoelectric effect. A film is an aggregate structure formed so as to cover and adhere to a single side or both sides of a plate-like base (substrate). As illustrated in FIG. 1A, an electrode layer such as the first electrode 102 or an adjusting layer may be included between the substrate 101 and the piezoelectric film 103. As illustrated in FIG. 15A, the piezoelectric film 103 may directly cover the surface of the substrate 101. The thin film of the present invention refers to a film having a thickness measured in a direction perpendicular to a surface on which the film is formed, that is, a film thickness, of less than 10 μm, and having 20 or less grains stacked in the perpendicular direction. So-called piezoelectric ceramics formed through firing of a metal oxide as an independent formed body is not included in the piezoelectric film in the piezoelectric element according to the present invention.

Differently from the case of piezoelectric ceramics independent of a substrate, the piezoelectric film adheres to the substrate, and thus, is restrained by the substrate. Compressive stress or tensile stress in a film surface direction is produced in the piezoelectric film restrained by the substrate. In other words, the piezoelectric film in the piezoelectric element according to the present invention has residual stress in a direction parallel with the surface of the substrate. The residual stress suppresses change in crystal structure of the piezoelectric film when an external environment temperature changes. As a result, the piezoelectric film has a Curie temperature that is higher than that of piezoelectric ceramics having the same composition, and a practical temperature area is widened to a high temperature side.

Note that, the internal residual stress of the piezoelectric film is produced at a surface thereof adhering to the substrate, and thus, as the film thickness becomes larger, the internal residual stress becomes smaller. For example, when the piezoelectric film has a thickness of more than 10 μm, the effect of improving the Curie temperature produced by the internal residual stress cannot be expected.

Further, the piezoelectric film also has an advantage over piezoelectric ceramics in that fine patterning thereof can be carried out. When the piezoelectric film has a thickness of less than 10 μm, processing into a desired fine pattern can be easily carried out through patterning in film formation or etching after film formation.

(Perovskite-Type Metal Oxide)

The perovskite-type metal oxide of the present invention refers to a metal oxide having a perovskite structure that is ideally a cubic structure as described in "Iwanami Dictionary of Physics and Chemistry", Fifth Edition (Iwanami Shoten, published on Feb. 20, 1998).

The metal oxide having a perovskite structure is generally represented by a chemical formula of $ABO_3$. In the perovskite-type metal oxide, the elements A and B occupy specific positions in the form of ions in a unit cell, which are called A site and B site. For example, in a cubic unit cell, the element A is positioned at a vertex of the cube while the element B occupies the body-centered position of the cube. The element O occupies a face center position of the cube as an anion of oxygen.

In the metal oxide represented by the above-mentioned general formula (1), metal elements positioned in the A site are Ba and Ca, and metal elements positioned in the B site are Ti, Zr, and Sn.

A mole ratio of the elements at the B site to the element O in the general formula (1) described above is 1 to 3. Even when the ratio between the amounts of the elements deviates to some extent, for example, by 1% or less, insofar as a main phase of the metal oxide is the perovskite structure, such a case falls within the scope of the present invention.

A mole ratio of the element at the A site to the elements at the B site in the general formula (1) described above is 1 to 1. Even when the ratio of the element at the A site is in excess or falls short by a range of −5% to 20%, insofar as a main phase of the metal oxide is the perovskite structure, such a case falls within the scope of the present invention. However, it is preferred that the composition of the general formula (1) be uniform in the piezoelectric film, and it is preferred that variations in A-site elements/B-site elements among locations in the piezoelectric film be 1% or less.

It can be determined that the metal oxide has the perovskite structure through, for example, X-ray diffraction or electron diffraction on the piezoelectric film. Insofar as a main crystal phase is the perovskite structure, the piezoelectric film may secondarily include other crystal phases.

(Principal Component of Piezoelectric Film)

When the piezoelectric film forming the piezoelectric element according to the present invention includes an oxide containing Ba, Ca, Ti, and Zr, and at least one element of Mn and Bi, $0.09 \leq x \leq 0.30$ is satisfied, where x is a mole ratio of Ca to a sum of Ba and Ca, $0.025 \leq y \leq 0.085$ is satisfied, where y is a mole ratio of Zr to a sum of Ti, Zr, and Sn, and $0 \leq z \leq 0.02$ is satisfied, where z is a mole ratio of Sn to the sum of Ti, Zr, and Sn, excellent piezoelectric properties are exhibited.

More specifically, when $(Ba, Ca)(Ti, Zr, Sn)O_3$ expressed by the general formula (1) is the principal component, in a temperature range in which the piezoelectric element is used, for example, in a temperature range of from −30° C. to 50° C., a sufficiently high piezoelectric constant can be obtained.

In the general formula (1), a range of x representing the mole ratio of Ca to the sum of a Ba content and a Ca content is 0.09≤x≤0.30.

When the Ca amount x is smaller than 0.09, a phase transition temperature from a tetragonal to an orthorhombic (hereinafter $I_{to}$) is higher than −10° C., and, as a result, change in piezoelectric constant with respect to temperature in the temperature range in which the piezoelectric element is used (for example, from −30° C. to 50° C.) increases. On the other hand, when x is larger than 0.30, the piezoelectric constant decreases in the entire temperature range in which the piezoelectric element is used. From the viewpoint of obtaining a higher piezoelectric constant, x≤0.20 is preferred, and x≤0.17 is further preferred.

As described above, as the Ca content increases, the piezoelectric constant tends to decrease in the temperature range in which the piezoelectric element is used.

In the general formula (1), y representing the mole ratio of Zr to the sum of a Ti content, a Zr content, and a Sn content is 0.025≤y≤0.085.

When the Zr amount y is smaller than 0.025, the piezoelectric constant decreases in the entire temperature range in which the piezoelectric element is used. On the other hand, when y is larger than 0.085, a Curie temperature (hereinafter $T_c$) is lowered, for example, $T_c$ is lower than 90° C. When $T_c$ is lowered, a dielectric loss of the piezoelectric element at, for example, 50° C. increases, and the piezoelectric constant decreases while the piezoelectric element is continuously driven. From the viewpoint of obtaining a higher piezoelectric constant, a more preferred range of y is 0.040≤y≤0.085.

In the general formula (1), z representing the mole ratio of Sn to the sum of the Ti content, the Zr content, and the Sn content is 0≤z≤0.02. Substitution of Sn for Ti is, similarly to substitution of Zr for Ti, made for the purpose of increasing the piezoelectric constant of the piezoelectric element due to increase in permittivity at room temperature. However, when Ti is substituted with a large amount of Zr or a large amount of Sn, $T_{to}$ of the piezoelectric element increases. When $T_{to}$ is within the temperature range in which the piezoelectric element is used, change in the piezoelectric constant with respect to temperature increases. Therefore, according to the present invention, Ca having the effect of reducing dependence of the piezoelectric constant on temperature is added to cancel change in $T_{to}$.

On the other hand, when attention is paid to a difference between Sn and Zr, when Ti is substituted with Sn, an extent of increase in $T_{to}$ is smaller than that when Ti is substituted with Zr. For example, when 1% of Ti in BaTiO$_3$ is substituted with Zr, $T_{to}$ increases by about 12° C., and, when 1% of Ti is substituted with Sn, $T_{to}$ increases by about 5° C. Therefore, the Ca amount can be reduced when Ti is substituted with Sn. However, when z is larger than 0.02, depending on the Zr amount, there is a case in which $T_c$ is lower than 100° C.

A method of measuring the composition of the piezoelectric film according to the present invention is not particularly limited. Exemplary methods include X-ray fluorescence analysis (XRF), ICP-atomic emission spectrometry (ICP-AES), and atomic absorption spectroscopy (AAS). Weight ratios and composition ratios of elements contained in the piezoelectric film can be calculated by any one of those methods. A particularly preferred measurement method for the composition is XRF.

For the purpose of facilitating manufacture of the piezoelectric film or adjusting physical properties of the piezoelectric film according to the present invention, 1 mol % or less of Ba and Ca may be substituted with a divalent metal element, for example, Sr. Similarly, 1 mol % or less of Ti, Zr, and Sn may be substituted with a tetravalent metal element, for example, Hf.

(First Auxiliary Component of Piezoelectric Film)

The piezoelectric film includes a first auxiliary component containing at least one of Mn and Bi. A total content $S_{ave}$ of Mn and Bi is 0.0020 moles or more and 0.0150 moles or less for 1 mole of the metal oxide (Ba, Ca) (Ti, Zr, Sn)O$_3$. With regard to the composition of the entire film, it is not necessarily required to examine the composition of all portions of the film, and a representative value obtained by measuring, with XRF, a major area except for end portions of the film at one time may be used. From contents of metals obtained through composition analysis of the piezoelectric film, elements forming the metal oxide expressed by the general formula (1) are converted to moles, and the total number of moles is taken as 1. Then, a molar amount of the first auxiliary component can be calculated.

Through inclusion of at least one of Mn and Bi in the piezoelectric film in the range described above, site deficits are compensated for, and thus, a piezoelectric constant in the range of from −30° C. to 50° C. of the piezoelectric element according to the present invention is improved to suppress a dielectric loss. Further, reduction of the piezoelectric constant while the piezoelectric element is continuously driven can be suppressed.

When the total content $S_{ave}$ is smaller than 0.0020 moles, difference in physical properties from a case in which Mn or Bi is not contained is small, and thus, the effects described above cannot be fully obtained. On the other hand, when the total content $S_{ave}$ is larger than 0.0150 moles, the dielectric loss of the piezoelectric element abruptly increases. When the dielectric loss of the piezoelectric element is, for example, more than 1.5% (measurement frequency of 1 kHz), there are problems in that heat is generated and that power consumption increases when the piezoelectric element is used.

When the piezoelectric film contains both Mn and Bi, the piezoelectric constant is further increased, which is more preferred. A preferred content of single-component Mn is 0.002 moles or more and 0.008 moles or less for 1 mole of the metal oxide, and a preferred content of single-component Bi is 0.001 moles or more and 0.005 moles or less for 1 mole of the metal oxide.

Mn and Bi are not limited to single-component metals. Mn or Bi only needs to be contained in the piezoelectric film as a Mn component or a Bi component, and how Mn or Bi is contained does not matter.

(Other Auxiliary Components of Piezoelectric Film)

It is preferred that the piezoelectric film contain the perovskite-type metal oxide expressed by the general formula (1) and the first auxiliary component such that a total amount thereof is 98.5 mol % or more. Further, it is preferred that the piezoelectric film contain the perovskite-type metal oxide expressed by the general formula (1) as the principal component by 95 mol % or more.

(Thickness of Piezoelectric Film)

It is preferred that a thickness of a portion of the piezoelectric film 103 sandwiched between the first electrode 102 and the second electrode 104, or, of a portion of the piezoelectric film 103 sandwiched between the substrate 101 and the comb electrodes 105 be 500 nm or more and 10 μm or less. It is more preferred that the thickness be 500 nm or more and 5,000 nm or less.

When the film is not planar, the thickness is measured in a perpendicular direction with the surface of the substrate 101 being a base. When the thickness is not constant, an average of a maximum value and a minimum value is regarded as the thickness. Through setting of the thickness of the piezoelectric film 103 to be 500 nm or more and 5,000 nm or less, a function of the piezoelectric element can be obtained, and processability of the piezoelectric film for forming a piezoelectric element can be attained.

When the thickness of the piezoelectric film 103 is smaller than 500 nm, a sufficient piezoelectric constant may not be obtained. On the other hand, when the thickness of the piezoelectric film 103 is larger than 5,000 nm, processability as a thin film piezoelectric element may be insufficient.

It is more preferred that the thickness of the piezoelectric film 103 be 700 nm or more and 4,000 nm or less, and it is further preferred that the maximum film thickness $T_p$ of the piezoelectric film 103 be 1,000 nm or more and 3,500 nm or less.

The thickness of the piezoelectric film 103 can be measured with a contact profilometer or through observation of a section thereof under a microscope.

(First Auxiliary Component in Region Adjacent to One Electrode)

A total content $S_{bou}$ of Mn and Bi in a region of the piezoelectric film 103 adjacent to one electrode is smaller than $S_{ave}$. As illustrated in FIG. 1B, a region 1031 adjacent to one electrode refers to a portion of the piezoelectric film in the vicinity of the electrode. According to the present invention, the piezoelectric film 103 has a configuration in which, in a thickness direction, a relatively large amount of a first auxiliary component exists in an imbalanced manner in a center portion and a concentration of the first auxiliary component is lowered toward an electrode. Therefore, there is no problem insofar as a thickness of the region adjacent to one electrode is 49% or less of the thickness of the piezoelectric film 103 with the electrode being the base. However, in order to more quantitatively conduct verification, it is preferred that the region 1031 adjacent to one electrode be assumed to be in a layer form in contact with the electrode and a thickness of the layer be nm or more and 5% or less of the thickness of the piezoelectric film 103 when $S_{bou}$ is determined. In that case, it is preferred that the relationship satisfy $0\% \le S_{bou}/S_{ave} \le 10\%$.

When $S_{bou}$ is smaller than $S_{ave}$, the effect of compensating for site deficits by Mn or Bi is attained in the piezoelectric film as a whole, and, locally, undesired bonding reaction between the first auxiliary component (at least one of Mn and Bi) and a metal electrode in the vicinity of the electrode can be suppressed. From this viewpoint, it is ideal that $S_{bou}/S_{ave}$ be as small as possible.

"One electrode" as used herein refers to an electrode in contact with a surface of the piezoelectric film such as the first electrode 102, the second electrode 104, and the comb electrode 105. When $S_{bou}$ is smaller than $S_{ave}$ in the regions 1031 adjacent to all the electrodes formed so as to sandwich the piezoelectric film, the effects of the present invention are maximized, which is more preferred.

A concentration distribution of the first auxiliary component is for the purpose of suppressing reaction with the metal electrodes, and thus, it is desired that the concentration be distributed only in the thickness direction. In other words, it is preferred that the concentration of the first auxiliary component be uniform in a film surface direction. For example, it is preferred that variations in the concentration of the first auxiliary component in the film surface direction for 1 mole of the metal oxide as the principal component be 0.001 moles or less.

A local Mn content and a local Bi content in the piezoelectric film 103 can be specified through composition analysis such as energy dispersive X-ray spectroscopy (EDX or EDS) or electron energy loss spectroscopy (EELS) with regard to a section of the piezoelectric film under a scanning electron microscope (SEM) or a transmission electron microscope (TEM).

(Principal Component in Region Adjacent to One Electrode)

According to the present invention, as described above, a configuration is intended in which, in the thickness direction, a relatively large amount of the first auxiliary component exists in an imbalanced manner in the center portion, and the concentration of the first auxiliary component is lowered toward an electrode. However, it is preferred that a composition distribution of the principal component be uniform in the thickness direction. Specifically, in a region of the piezoelectric film 103 adjacent to one electrode, when a local composition of Ba, Ca, Ti, Zr, and Sn is expressed by a general formula (2), it is preferred that $|x-x'| \le 0.02$, $|y-y'| \le 0.01$, and $|z-z'| \le 0.01$.

$$(Ba_{1-x}Ca_{x'})(Ti_{1-y'-z'}Zr_{y'}Sn_{z'})O_3 \quad (2)$$

It is preferred that "a region of the piezoelectric film adjacent to one electrode" be the same when verification is conducted with regard to the first auxiliary component and when verification is conducted with regard to the principal component.

When a difference between x and x' is larger than 0.02, change in properties of the piezoelectric element with respect to temperature may be excessively large. When a difference between y and y' is larger than 0.01, the piezoelectric constant may be below a practical level. When a difference between z and z' is larger than 0.01, the piezoelectric constant may be below a practical level.

A local content of the principal component in the piezoelectric film 103 can be specified through composition analysis such as EDX or EELS with regard to a section of the piezoelectric film under a SEM or a TEM.

(Adhesion Component)

Figure 2A:
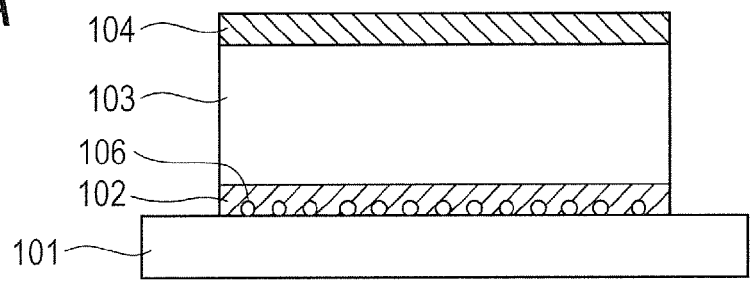
FIG. 2A, FIG. 2B, and FIG. 2C are schematic sectional views for illustrating configurations of the piezoelectric element according to an embodiment of the present invention.
Figure 2B:
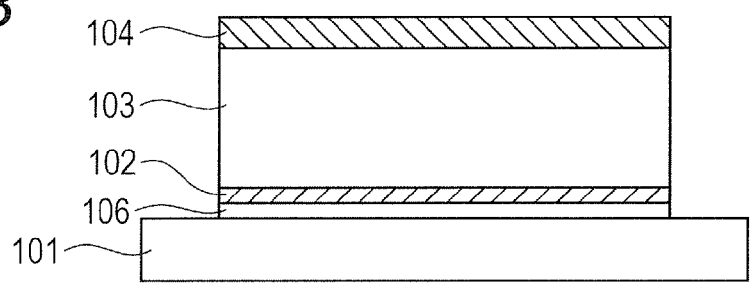

It is preferred that an adhesion component containing a metal of Group 4 elements and/or Group 5 elements exists between the first electrode and the substrate. FIG. 2A and FIG. 2B are schematic sectional views of the piezoelectric element according to the present invention when the adhesion component 106 exists between the substrate 101 and the first electrode 102.

The adhesion component may exist so as to be dispersed in a dot-like manner and so as to be embedded in the first electrode as the adhesion component 106 illustrated in FIG. 2A, or may be in the shape of a layer having a thickness of 1 nm or more and 10 nm or less as the adhesion component 106 in the shape of a layer illustrated in FIG. 2B.

It is preferred that a material of the adhesion component 106 be a single-component metal, an oxide, or a nitride of Ti, Zr, or Hf of Group 4 elements, or be a single-component metal, an oxide, or a nitride of V, Nb, or Ta of Group 5 elements from the viewpoint of adhesion. Part or the entirety of the adhesion component 106 may be chemically bonded to the substrate 101 or the first electrode 102 to form an alloy or a complex oxide.

(Crystal Structure of Piezoelectric Film)

Figure 2C:
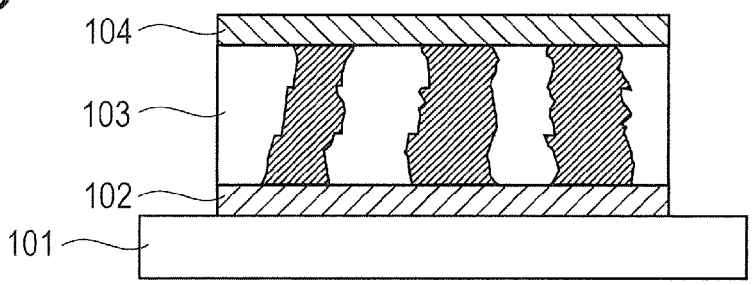

The piezoelectric film 103 according to the present invention is a thin film-like crystalline aggregate, and it is preferred that the crystalline aggregate have an aggregate structure formed of grains each having a columnar structure. FIG. 2C is a schematic sectional view of a piezoelectric element having an aggregate structure formed of grains each having a columnar structure in the piezoelectric film 103. In FIG. 2C, each of the finely shaded region and the uncolored region in the piezoelectric film 103 indicates a grain having a columnar structure.

That a grain is a columnar crystal can be confirmed through observation of a section of the piezoelectric film portion of the piezoelectric element under a microscope. In most cases, a grain having a columnar structure and another grain adjacent to that grain have crystal orientations different from each other, and thus, a grain boundary can be determined from contrast in an image under a microscope.

An aggregate structure refers to a state in which at least two grains are adjacent to each other, and it is preferred that substantially an entire region of a section of the piezoelectric film 103 be formed of an aggregate of columnar crystals.

It is preferred that a grain having a columnar structure be a single grain in contact with both the first electrode 102 and the second electrode 104. In the case of the second embodiment of the piezoelectric element, it is preferred that a grain be a single grain in contact with both the substrate 101 and the comb electrode 105.

It is preferred that a grain size on the surface of the piezoelectric film 103 be 300 nm or more and 5,000 nm or less as an average equivalent circle diameter. When the grain size is smaller than 300 nm, the piezoelectric constant of the piezoelectric element may be insufficient in the range of from −30° C. to 50° C. On the other hand, when the grain size is larger than 5,000 nm, the processability as the thin film type piezoelectric element may be insufficient.

The "equivalent circle diameter" used herein refers to a "projected area equivalent circle diameter" that is generally mentioned in a microscopic observation method and indicates a diameter of a perfect circle having the same area as a projected area of the crystal grain. In the present invention, the method of measuring the equivalent circle diameter is not particularly limited. For example, the equivalent circle diameter can be determined by photographing a surface of the piezoelectric material using a polarizing microscope or a scanning electron microscope, and by performing image processing on the obtained photographic image. The optimum magnification varies depending on the particle diameter to be observed, and hence an optical microscope or an electron microscope may be used appropriately. An equivalent circle diameter may be determined from an image of a polished surface or a section instead of a surface of a material. An average equivalent circle diameter refers to an average of equivalent circle diameters of a plurality of grains.

(Curie Temperature)

It is preferred that the piezoelectric film in the piezoelectric element according to the present invention have a Curie temperature of 121° C. or higher. When the piezoelectric film has a Curie temperature of 121° C. or higher, that can be said to be sufficiently separate from the operating temperature range of the piezoelectric device (−30° C. to 50° C.). Thus, the influence of abrupt temperature change on the piezoelectric constant and the dielectric loss of the piezoelectric element in the vicinity of the Curie temperature can be neglected in the operating temperature range of the piezoelectric device.

A more preferred range of the Curie temperature of the piezoelectric film is 130° C. or higher and 195° C. or lower. When the temperature is the Curie temperature or higher, piezoelectricity of a piezoelectric material disappears. As used herein, the Curie temperature refers to a temperature at which a capacitance is at a maximum in the vicinity of the phase transition temperature between a ferroelectric phase (tetragonal phase) and a paraelectric phase (cubic phase). The capacitance is measured through, for example, application of a minute AC electric field having a frequency of 1 kHz using an impedance analyzer.

(Orientation)

It is preferred that a crystal forming the perovskite structure of the piezoelectric film in the piezoelectric element according to the present invention be selectively oriented in the direction perpendicular to the surface of the substrate. With regard to an orientation plane, it is preferred that a crystal be selectively oriented in a (100) plane, a (110) plane, or a (111) plane when a unit cell of the perovskite structure is regarded as a pseudo cubic crystal.

"Selectively oriented in an (hkl) plane" as used herein refers to a state in which a degree of orientation in the (hkl) plane is higher than degrees of orientation in other planes. This can also be described as "preferentially oriented in the (hkl) plane" and also includes a state in which a crystal is completely oriented in the (hkl) plane as in the case of a monocrystal.

When the piezoelectric film is oriented in the (100) plane, the (110) plane, or the (111) plane, a direction of polarization moment aligns with a direction of the strain on the piezoelectric film, and thus, the piezoelectric constant at each temperature increases.

The state of orientation of the piezoelectric film can be easily confirmed from a detected angle and a strength of a diffraction peak in X-ray diffraction measurement that is generally used for a crystal thin film (for example, 2θ/θ method). For example, in a diffraction chart obtained from a piezoelectric film oriented in any one of the planes, a strength of a diffraction peak detected at an angle corresponding to the plane is exceedingly higher than a total of strengths of peaks detected at angles corresponding to other planes.

(Methods of Manufacturing Piezoelectric Element and Piezoelectric Film)

A method of manufacturing the piezoelectric film portion in the piezoelectric element is not particularly limited. Exemplary methods include CSD, sputtering, hydrothermal synthesis, aerosol deposition, and metal organic chemical vapor deposition (MOCVD). In any of the manufacturing methods, by setting a concentration of the sum of Mn and Bi in the material used for the portion of the piezoelectric film in the vicinity of an electrode to be lower than the concentration of the sum of Mn and Bi in the material of the piezoelectric film in other portions, the piezoelectric element according to the present invention can be manufactured. Among them, CSD and sputtering are preferred manufacturing methods, and are excellent in controlling the composition of the piezoelectric film.

When the piezoelectric film is formed by CSD, it is preferred that the method of manufacturing a piezoelectric element include:

(a) applying a first raw material liquid onto a substrate having a first electrode layer formed on a surface thereof to form an applied layer;

(b) firing the applied layer every time the applied layer is formed to form a piezoelectric body layer, the steps (a) and (b) being conducted once or a plurality of times to form a piezoelectric film lower layer;

(c) applying a second raw material liquid onto the piezoelectric film lower layer to form an applied layer;

(d) firing the applied layer every time the applied layer is formed to form a piezoelectric body layer, the steps (c) and (d) being conducted once or a plurality of times to form a piezoelectric film intermediate layer;

(e) applying a third raw material liquid onto the piezoelectric film intermediate layer to form an applied layer;

(f) firing the applied layer every time the applied layer is formed to form a piezoelectric body layer, the steps (e) and (f) being conducted once or a plurality of times to form a piezoelectric film upper layer; and (g) forming a second electrode layer on a surface of the piezoelectric film upper layer to manufacture the piezoelectric element, in which the second raw material liquid includes Ba, Ca, Ti, and Zr, and includes at least one of Mn and Bi, and in which the first raw material liquid and the third raw material liquid include Ba, Ca, Ti, and Zr, with a concentration of a sum of Mn and Bi therein being 1,000 ppm or less.

FIG. 1C is a schematic view for illustrating an exemplary configuration of the piezoelectric element according to the present invention. When the piezoelectric film 103 is formed by CSD, the piezoelectric film 103 can be classified into a piezoelectric film lower layer 1032 adjacent to the first electrode 102, a piezoelectric film upper layer 1034 adjacent to the second electrode 104, and a piezoelectric film intermediate layer 1033 that does not correspond to either of those two. However, borders between the piezoelectric film lower layer 1032 and the piezoelectric film intermediate layer 1033 and between the piezoelectric film intermediate layer 1033 and the piezoelectric film upper layer 1034 are only distinguished during manufacture, and, after the piezoelectric element is completed, the three layers are integrated as the piezoelectric film 103. Regions of the piezoelectric film lower layer 1032 and the piezoelectric film upper layer 1034 determined by timing of changing a raw material type during manufacture and the regions 1031 adjacent to the electrodes, respectively, illustrated in FIG. 1B that are defined in verification after the piezoelectric element is completed are not necessarily required to be spatially coincident.

It is preferred that a thickness of the piezoelectric film lower layer 1032 be smaller than a thickness of the piezoelectric film intermediate layer 1033. Similarly, it is preferred that a thickness of the piezoelectric film upper layer 1034 be smaller than the thickness of the piezoelectric film intermediate layer 1033.

It is preferred that the number of repetitions of the steps (a) and (b) be smaller than the number of repetitions of the steps (c) and (d). Similarly, it is preferred that the number of repetitions of the steps (e) and (f) be smaller than the number of repetitions of the steps (c) and (d).

As a solvent of the first, second, and third raw material liquids, an organic solvent such as an alcohol-based one can be used. For the purpose of assisting dissolution or dispersion of a metal component, a stabilizer such as an amine may be contained in the raw material liquid.

The first, second, and third raw material liquids may contain Sn as necessary. In the first, second, and third raw material liquids, it is preferred that Ba, Ca, Ti, and Zr be, in terms of the metal oxide expressed by the general formula (1), 15 wt % or more and 30 wt % or less. It is more preferred that the concentration of the sum of Mn and Bi in the first and third raw material liquids be 500 ppm or less, and it is further preferred that the concentration be 200 ppm or less.

"ppm" as used herein relating to a concentration of a metal component in the raw material liquids means the weight of the metal component as a single-component metal expressed in mg that is contained in 1 kg of a solution.

On the other hand, it is preferred that the concentration of the sum of Mn and Bi in the second raw material liquid be 0.002 moles or more and 0.02 moles or less when the molar amount of the sum of Ti and Zr is 1 mole. Further, it is preferred that, under a state in which the concentration of the sum of Mn and Bi is 0.002 moles or more and 0.02 moles or less, the concentration of single-component Mn be 0.002 moles or more and 0.012 moles or less and the concentration of single-component Bi be 0.001 moles or more and 0.008 moles or less.

Exemplary methods of forming the applied layers include spin coating and dip coating.

Heat treatment at from 200° C. to 450° C. for the purpose of removing an organic component may be provided between a step of forming an applied layer and a step of firing the applied layer. It is preferred that a firing temperature be about from 600° C. to 850° C. It is preferred to perform, after applying a final layer in the step (f), firing at a temperature higher than before, for example, from 650° C. to 900° C.

Exemplary formation of the piezoelectric film 103 by sputtering is as follows. A first step is preparing two kinds of targets having different compositions. A target used for forming the piezoelectric film lower layer 1032 and the piezoelectric film upper layer 1034 contains at least Ba, Ca, Ti, and Zr, and the total content of Mn and Bi in the target is 1,000 ppm or less. On the other hand, a target used for forming the piezoelectric film intermediate layer 1033 contains at least Ba, Ca, Ti, and Zr, and contains at least one of Mn and Bi. The two kinds of targets contain Sn as necessary. The metal components may be contained in one target as a sintered body, or may be divided into a plurality of targets each alone or in a mixed state.

In a second step, the two kinds of targets are selectively used to form the piezoelectric film lower layer 1032, the piezoelectric film intermediate layer 1033, and the piezoelectric film upper layer 1034 in this order to obtain the intended piezoelectric film 103. Film formation by sputtering is a step of placing, in a decompression chamber, the two kinds of targets and the substrate 101 or the substrate 101 having the first electrode 102 formed thereon and causing high energy particles (such as ionized inert gas particles) to collide against a surface of any one of the targets to form the intended piezoelectric film 103 on the surface of the substrate 101 or the first electrode 102. For the purpose of accelerating crystallization, the substrate 101 may be heated in the chamber, or heat treatment may be performed outside the chamber after the piezoelectric film is formed.

(Piezoelectric Actuator)

A piezoelectric actuator according to the present invention includes the piezoelectric element according to the present invention and a diaphragm formed in contact with the piezoelectric element.

Figure 3A:
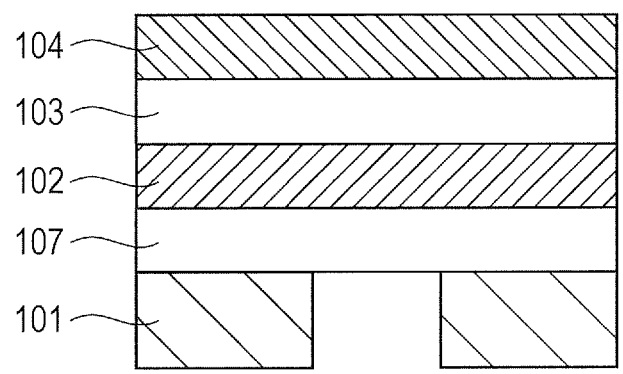
FIG. 3A and FIG. 3B are a schematic sectional view and a schematic rear view, respectively, for illustrating a configuration of a piezoelectric actuator according to an embodiment of the present invention.
Figure 3B:
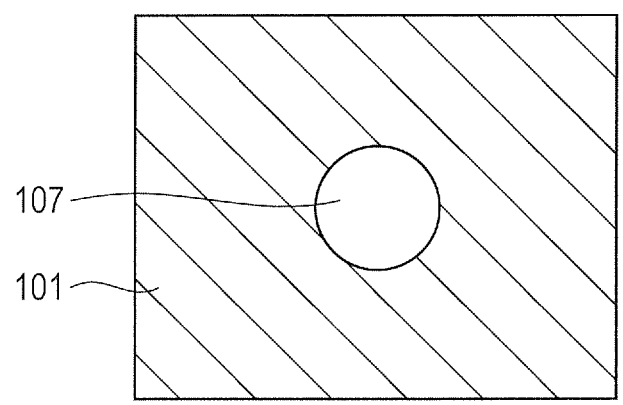

FIG. 3A and FIG. 3B are a schematic sectional view and a schematic rear view, respectively, for illustrating a piezoelectric actuator according to an embodiment of the present invention. In the case illustrated in FIG. 3A and FIG. 3B, a diaphragm 107 is formed in contact with the first electrode 102 and the substrate 101 of the piezoelectric element according to the present invention.

The diaphragm 107 has a thickness of 1.0 μm or more and 15 μm or less. A more preferred thickness thereof is 1.5 μm or more and 8 μm or less.

A material forming the diaphragm 107 is not particularly limited, and a metal material, a metal oxide material, a glass-based material, or the like is used. A more preferred material of the diaphragm 107 is $SiO_2$ (silicon dioxide).

A method of manufacturing the diaphragm 107 is not particularly limited. For example, oxidation treatment may be performed to the substrate 101 to modify the surface thereof, or a material forming the diaphragm 107 may be bonded to the substrate 101. The diaphragm 107 may be formed by CSD, sputtering, hydrothermal synthesis, aerosol deposition, MOCVD, or the like, or a surface portion of the substrate 101 may also serve as the diaphragm 107.

In the piezoelectric actuator according to the present invention, when a voltage is applied between the first electrode 102 and the second electrode 104, the piezoelectric film 103 is deformed. The deformation is amplified by the effect of the diaphragm 107 adhering to the piezoelectric element. As a result, the piezoelectric actuator according to the embodiment illustrated in FIG. 3A and FIG. 3B undergoes displacement to a great extent in a hole portion in the substrate 101. An amount of the displacement can be easily controlled with the voltage and a frequency.

(Liquid Ejection Head)

Next, a liquid ejection head according to the present invention is described.

The liquid ejection head according to the present invention includes a liquid chamber including a vibration portion containing the above-mentioned piezoelectric element, and an ejection orifice communicating with the liquid chamber.

Figure 4A:
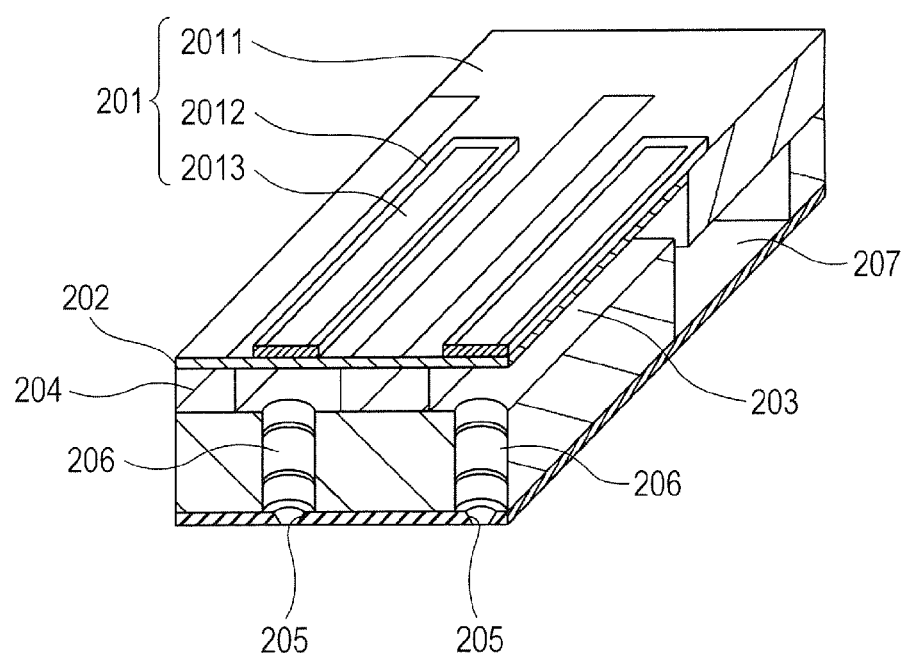
FIG. 4A and FIG. 4B are schematic views for illustrating configurations of a liquid ejection head and a liquid ejection apparatus according to embodiments, respectively, of the present invention.

FIG. 4A is a schematic view for illustrating a configuration of the liquid ejection head according to an embodiment of the present invention. Shapes and arrangements of members are not limited to those illustrated in FIG. 4A. A piezoelectric element 201 includes at least a first electrode 2011, a piezoelectric film 2012, and a second electrode 2013. In the case illustrated in FIG. 4A, a substrate as one member forming the piezoelectric element according to the present invention also serves as a liquid chamber division wall 204. The piezoelectric film 2012 and the second electrode 2013 are patterned for the purpose of enhancing ejection force of the liquid ejection head.

The liquid ejection head includes ejection orifices 205, individual liquid chambers 203, communicating holes 206 connecting the individual liquid chambers 203 and the ejection orifices 205, respectively, the liquid chamber division wall 204, a common liquid chamber 207, a diaphragm 202, and piezoelectric elements 201. An adhesion component may exist between the diaphragm 202 and the first electrode 2011. A material and a thickness suitable for the diaphragm 202 are similar to those for the diaphragm 107 in the piezoelectric actuator.

In the liquid ejection head of the present invention, the diaphragm 202 vertically vibrates owing to the deformation of the piezoelectric element 201 to apply a pressure to liquid stored in the individual liquid chamber 203. As a result, the liquid is ejected from the ejection orifice 205. The liquid ejection head of the present invention can be used in a printer application or the production of an electronic device.

(Liquid Ejection Apparatus)

Next, a liquid ejection apparatus of the present invention is described. The liquid ejection apparatus of the present invention includes a mounting unit of a transfer target, and the liquid ejection head.

Figure 4B:
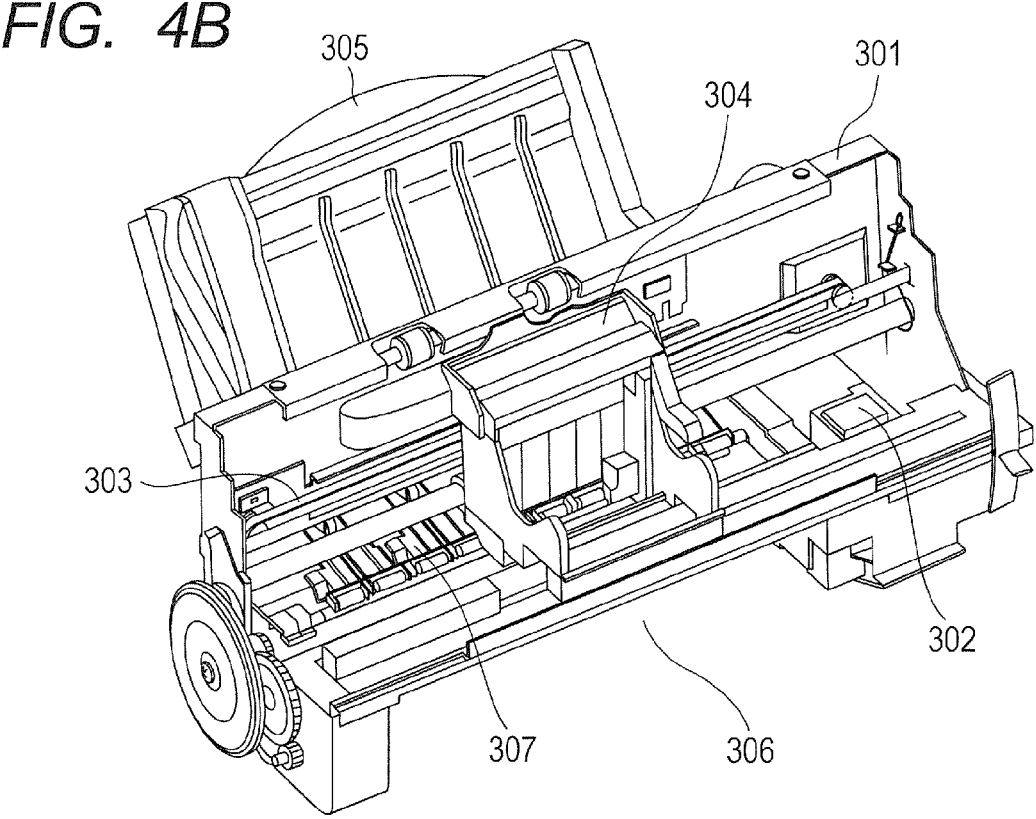

An ink jet recording apparatus illustrated in FIG. 4B is an exemplary liquid ejection apparatus according to the present invention. In the ink jet recording apparatus (liquid ejection apparatus), mechanisms are incorporated into an exterior unit 301. An automatic feeding unit 305 has a function of automatically feeding a recording sheet as a transfer target into an apparatus body. The recording sheet fed from the automatic feeding unit 305 is introduced by a conveying unit 307 to a predetermined recording location (no reference number), and, after recording operation, is again introduced by the conveying unit 307 from the recording location to an ejection unit 306. The conveying unit 307 corresponds to a placing portion for a transfer target.

In addition, the ink jet recording apparatus includes a recording unit 303 configured to perform recording on the recording sheet conveyed to the recording location and a recovering unit 302 configured to conduct recovery processing for the recording unit 303. The recording unit 303 includes a carriage 304 configured to house the liquid ejection head therein and to reciprocate the liquid ejection head on a rail.

In the ink jet recording apparatus described above, the carriage 304 conveys the liquid ejection head under instruction from an external computer and ink is ejected through ejection orifices of the liquid ejection head based on a voltage applied to the piezoelectric film, to thereby perform printing.

In the above, a case of a printer is described, but the liquid ejection apparatus according to the present invention can be used as, other than printing apparatus such as ink jet recording apparatus including a facsimile machine, a multifunction device, and a copying machine, an industrial liquid ejection apparatus and a device for drawing a picture on a target. In addition, a user can select a desired transfer target depending on a use.

(Vibration Correction Mechanism)

Next, a vibration correction mechanism according to the present invention is described. The vibration correction mechanism according to the present invention is a vibration correction mechanism that can reduce influence of a vibration applied from the outside while a transfer target is conveyed. The vibration correction mechanism includes two or more piezoelectric actuators described above, and the piezoelectric actuators are arranged such that, when a voltage is applied thereto, the piezoelectric actuators expand and contract in two or more directions. The vibration correction mechanism has such a configuration, and thus, influence of a vibration applied from the outside while a transport target is transported can be reduced.

Figure 5:
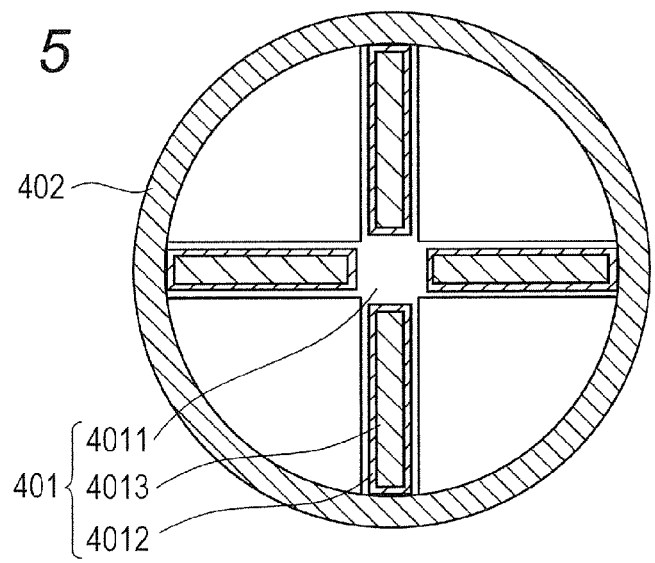
FIG. 5 is a schematic view for illustrating a configuration of a vibration correction mechanism according to an embodiment of the present invention.

FIG. 5 is a schematic view for illustrating a configuration of the vibration correction mechanism according to the present invention. Shapes and arrangements of members are not limited to those illustrated in FIG. 5. The vibration correction mechanism according to the present invention includes at least two piezoelectric actuators 401 and a transfer target 402. Each of the piezoelectric actuators 401 has structure in which a diaphragm 4011 also serving as a substrate, a first electrode (in FIG. 5, unseen at the back of a piezoelectric film), a piezoelectric film 4012, and a second electrode 4013 are laminated in this order.

In the case illustrated in FIG. 5, a plurality of piezoelectric elements are arranged on a cross-shaped common substrate. It is herein assumed that the vibration correction mechanism has four piezoelectric actuators 401 based on the number of the piezoelectric elements.

When an alternating voltage is applied to the four piezoelectric actuators 401 illustrated in FIG. 5 from an external voltage source, each of the piezoelectric actuators 401 expands and contracts in a longitudinal direction of the piezoelectric film 4012. Specifically, the piezoelectric actuators 401 expand and contract in two directions orthogonal to each other to transfer vibrations to the transfer target 402 in contact with the diaphragm 4011. Through combination of vibrations in the two directions, rotational motion of the transfer target 402 can be caused. When the rotational motion is caused so as to have a reverse phase with respect to the vibration applied from the outside, adverse influence of the vibration applied from the outside can be reduced.

The transfer target 402 may be a functional member that may be adversely influenced by a vibration applied from the outside, e.g., an optical member such as a lens or a mirror, or may be a connecting member configured to transfer the vibration to the functional member.

(Variable Optical Member)

Figure 6A:
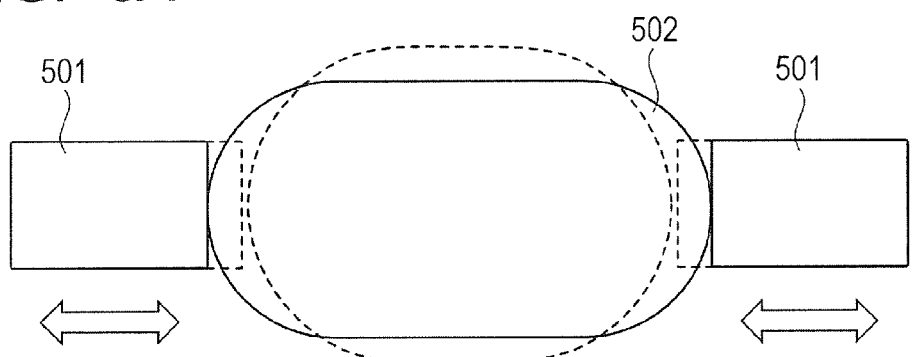
FIG. 6A and FIG. 6B are schematic views for illustrating configurations of a variable optical member and a movable optical member according to embodiments, respectively, of the present invention.

Next, a variable optical member according to the present invention is described. The variable optical member according to the present invention includes the piezoelectric actuators described above and an optical member dynamically connected to the piezoelectric actuators, and has a mechanism for changing a shape of the optical member through deformation of the piezoelectric actuators. FIG. 6A is a schematic view for illustrating a configuration of the variable optical member according to the present invention. Shapes and arrangements of members are not limited to those illustrated in FIG. 6A. The variable optical member according to the present invention includes piezoelectric actuators 501 and an optical member 502 whose shape is changed under the influence of deformation of the piezoelectric actuators 501. In the case illustrated in FIG. 6A, the piezoelectric actuators 501 and the optical member 502 are in contact with each other, thereby achieving dynamic connection between each of the piezoelectric actuators 501 and the optical member 502, but an intermediate member having a function of transferring deforming of the piezoelectric actuators 501 may be arranged between each of the piezoelectric actuators 501 and the optical member 502.

In the case illustrated in FIG. 6A, each of the two piezoelectric actuators 501 is dynamically connected to the optical member 502 at one location, but the numbers of the piezoelectric actuators 501 and the optical member 502 and connecting locations are not limited thereto.

Arrows in FIG. 6A are for illustrating extension and contraction of the piezoelectric actuators 501, and are not members. The optical member 502 is a member having a function of acting on properties of an optical path or a light beam such as a lens, a filter, or a mirror. For example, when a lens having a refractive index that is higher than that of air is used as the optical member 502, the shape of the optical member 502 can be changed depending on deformation of the piezoelectric actuators 501 to control a refracting angle of light passing through the lens.

(Movable Optical Member)

Next, a movable optical member according to the present invention is described. The movable optical member according to the present invention includes the piezoelectric actuators described above and an optical member dynamically connected to the piezoelectric actuators, and has a mechanism for moving and/or rotating the optical member through deformation of the piezoelectric actuators.

Figure 6B:
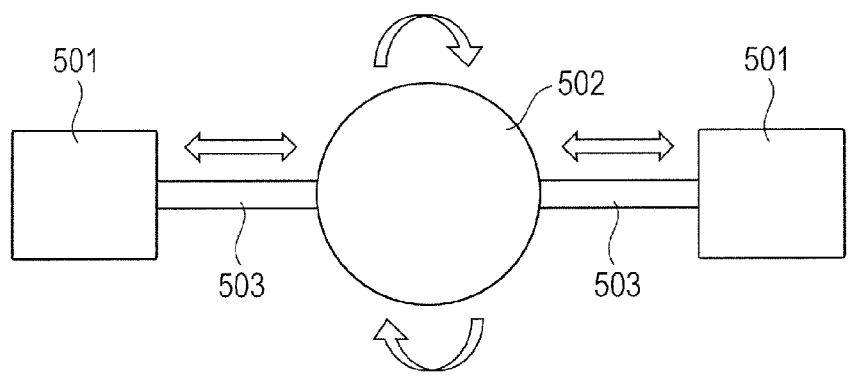

FIG. 6B is a schematic view for illustrating a configuration of the movable optical member according to the present invention. Shapes and arrangements of members are not limited to those illustrated in FIG. 6B. The movable optical member according to the present invention includes the piezoelectric actuators 501, the optical member 502 configured to be moved or rotated under the influence of deformation of the piezoelectric actuators 501, and piezoelectric strain transfer portions 503 configured to move or rotate the optical member 502 depending on deformation of the piezoelectric actuators 501.

In the case illustrated in FIG. 6B, the piezoelectric actuators 501 are in contact with the piezoelectric strain transfer units 503, respectively, and the piezoelectric strain transfer units 503 are in contact with the optical member 502, thereby making dynamic connection between each of the piezoelectric actuators 501 and the optical member 502. However, another intermediate member may be arranged between each of the piezoelectric actuators 501 and the optical member 502.

Arrows in FIG. 6B are for illustrating movement or rotation of the optical member 502, and are not members. The optical member 502 is a member having the function of acting on properties of an optical path or a light beam such as a lens, a filter, or a mirror. For example, when a mirror is used as the optical member 502, coordinates and an angle of the optical member 502 can be changed depending on deformation of the piezoelectric actuators 501 to control a direction of light reflected by the mirror.

(Optical Device)

Next, an optical device of the present invention is described.

A first embodiment of the optical device according to the present invention includes the vibration correction mechanism, and an optical member held by the vibration correction mechanism.

Figure 7A:
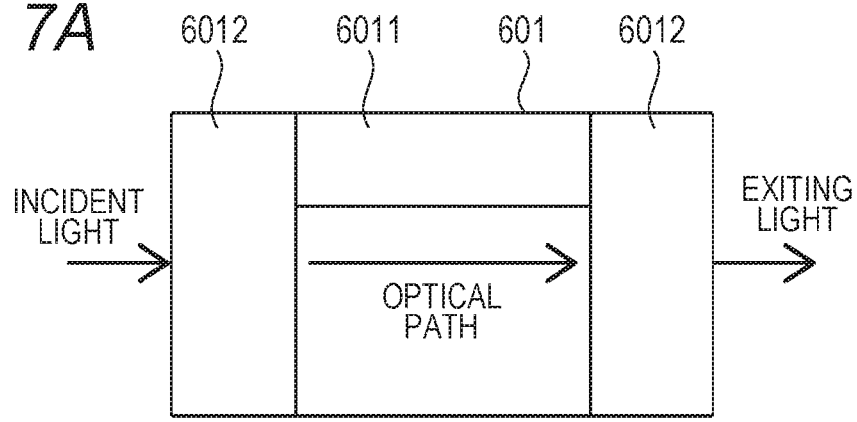
FIG. 7A, FIG. 7B, and FIG. 7C are schematic views for illustrating configurations of optical devices according to embodiments, respectively, of the present invention.

FIG. 7A is a schematic view for illustrating a configuration of an optical device 601 according to the present invention. The numbers and arrangements of members are not limited to those illustrated in FIG. 7A. The optical device according to the present invention includes a vibration correction mechanism 6011 and optical members 6012 as transport targets of the vibration correction mechanism 6011. A lens barrel connected to an image pickup apparatus when used is an example of the optical device. In this case, the optical members 6012 are lenses.

There is a problem in that, when a vibration such as a hand-induced vibration is applied from the outside to the optical device used as the lens barrel, an optical path of exiting light fluctuates during exposure time of the image pickup apparatus. This problem can be solved through suppression by the vibration correction mechanism 6011 of coordinate fluctuations of the optical members 6012. As illustrated in FIG. 7A, it is preferred that the vibration correction mechanism 6011 be arranged at a location at which the vibration correction mechanism 6011 does not interfere with the optical path passing through the optical members 6012.

A second embodiment of the optical device according to the present invention includes the variable optical member described above.

Figure 7B:
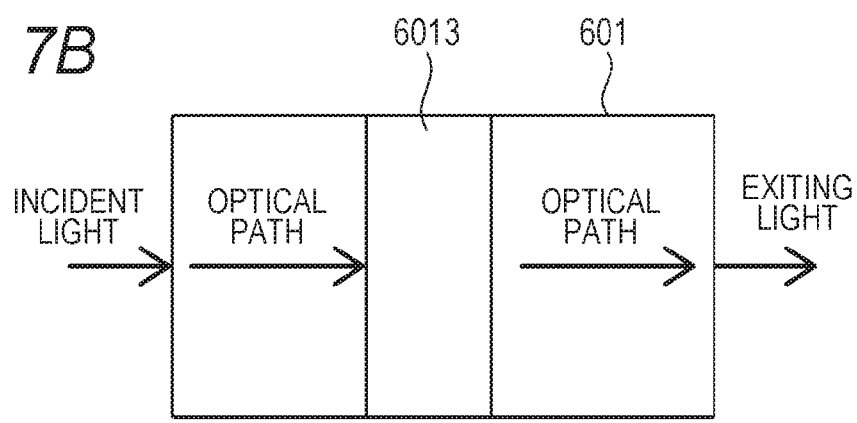

FIG. 7B is a schematic view for illustrating a configuration of the optical device 601 according to the present invention. The optical device according to the present invention includes at least a variable optical member 6013. The number and arrangement of the variable optical member 6013 are not limited to those illustrated in FIG. 7B. A lens barrel connected to an image pickup apparatus when used is an example of the optical device. In this case, the variable optical member 6013 is a variable lens. When a variable lens whose optical path can be controlled by a piezoelectric actuator is used, there is an effect that the number of lenses used in the lens barrel can be reduced. As illustrated in FIG. 7B, it is preferred that the variable optical member 6013 be arranged on an optical path of light incident on and exiting from the optical device.

A third embodiment of the optical device according to the present invention includes the movable optical member described above.

Figure 7C:
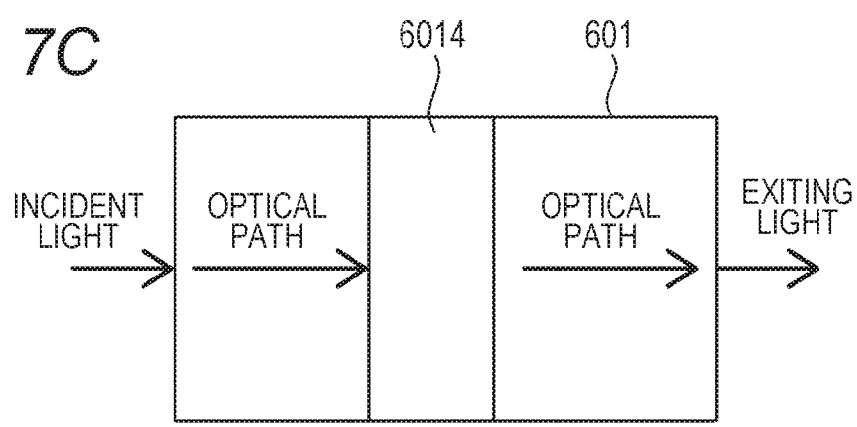

FIG. 7C is a schematic view for illustrating a configuration of the optical device 601 according to the present invention. The optical device according to the present invention includes at least a movable optical member 6014. The number and arrangement of the movable optical member 6014 are not limited to those illustrated in FIG. 7C.

A lens barrel connected to an image pickup apparatus when used is an example of the optical device. In this case, the movable optical member 6014 is a movable lens or a movable mirror. When a movable lens or a movable mirror whose optical path can be controlled by a piezoelectric actuator is used, there is an effect that the number of lenses used in the lens barrel can be reduced. As illustrated in FIG. 7C, it is preferred that the movable optical member 6014 be arranged on an optical path of light incident on and exiting from the optical device.

(Image Pickup Apparatus)

Next, an image pickup apparatus according to the present invention is described.

The image pickup apparatus according to the present invention includes the vibration correction mechanism described above, and an image pickup element unit held by the vibration correction mechanism.

Figure 8:
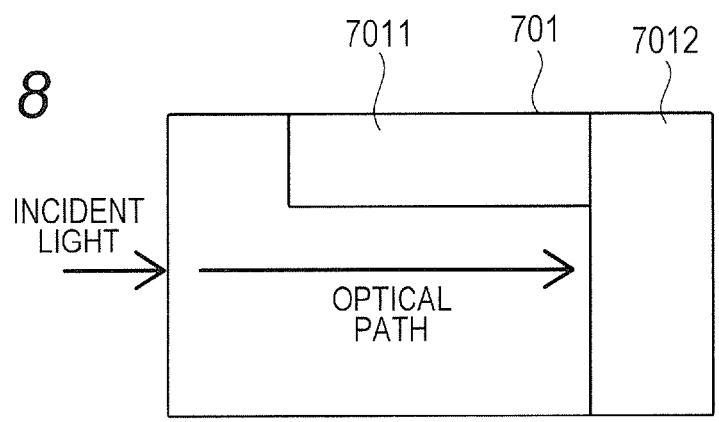
FIG. 8 is a schematic view for illustrating a configuration of an image pickup apparatus according to an embodiment of the present invention.

FIG. 8 is a schematic view for illustrating a configuration of the image pickup apparatus according to the present invention.

An image pickup apparatus 701 according to the present invention includes a vibration correction mechanism 7011 and an image pickup element unit 7012 as a transport target of the vibration correction mechanism 7011. The image pickup element unit 7012 is, for example, an electronic substrate having an image pickup element and an electrical element mounted thereon. Exemplary image pickup elements include a charge-coupled device (CCD) and a complementary metal oxide semiconductor (CMOS) image sensor.

There is a problem in that, when a vibration such as a hand-induced vibration is applied from the outside to the image pickup element unit 7012, image pickup data fluctuates during exposure time. This problem can be solved through suppression by the vibration correction mechanism 7011 of coordinate fluctuations of the image pickup element unit 7012. As illustrated in FIG. 8, it is preferred that the vibration correction mechanism 7011 be arranged at a location at which the vibration correction mechanism 7011 does not interfere with an optical path reaching a light receiving surface of the image pickup element unit 7012.

(Optical Switch)

Next, an optical switch according to the present invention is described.

A first embodiment of the optical switch according to the present invention includes the variable optical member described above.

Figure 9A:
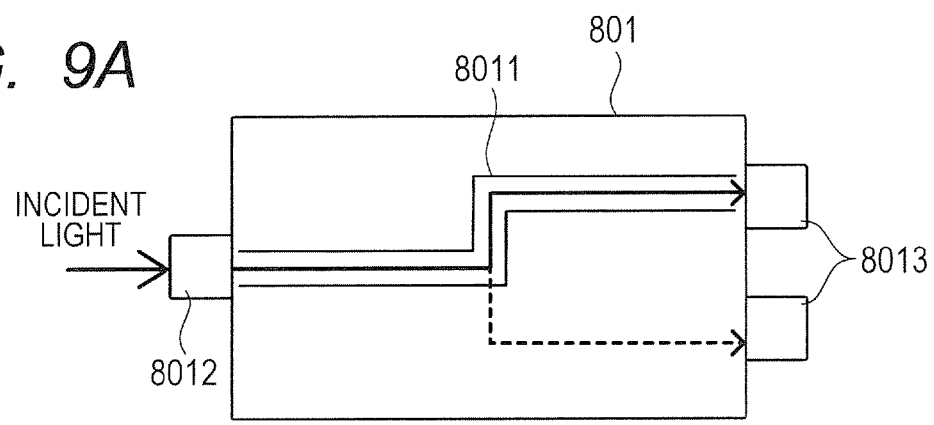
FIG. 9A and FIG. 9B are schematic views for illustrating configurations of optical switches according to embodiments, respectively, of the present invention.

FIG. 9A is a schematic view for illustrating a configuration of the optical switch according to the present invention. The numbers, shapes, and arrangements of members are not limited to those illustrated in FIG. 9A. An optical switch 801 according to the present invention includes a mechanism in which an optical path from an optical signal input terminal 8012 to an optical signal output terminal 8013 is changed under the influence of deformation of a variable optical member 8011.

FIG. 9A is an illustration of a case in which two optical signal output terminals 8013 are arranged, and, through switching of the optical signal output terminal 8013 that light reaches with the variable optical member 8011, on/off operation as a switch can be performed. In the case illustrated in FIG. 9A, the variable optical member 8011 includes a material having a light transmission property such as an optical fiber and a piezoelectric actuator.

A second embodiment of the optical switch according to the present invention includes the movable optical member described above.

Figure 9B:
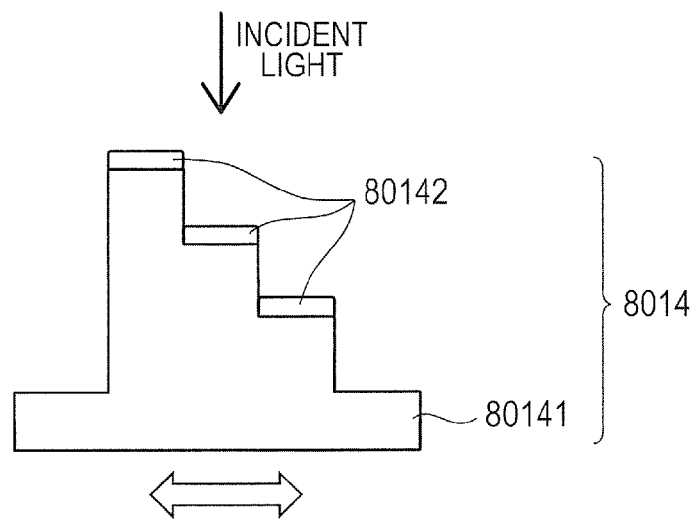

FIG. 9B is a schematic view for illustrating a configuration of the optical switch according to the present invention. The numbers, shapes, and arrangements of members are not limited to those illustrated in FIG. 9B. In the case illustrated in FIG. 9B, a movable optical member 8014 itself that includes a moving portion 80141 and a reflecting portion 80142 is an optical switch, but an optical switch may have a member other than the movable optical member 8014, for example, a slit or the like formed therein that is configured to limit a location irradiated with incident light.

The moving portion 80141 is a structure configured to move in a side-to-side direction in FIG. 9B under instructions from an external computer, and the reflecting portion 80142 is formed on surfaces on the incident light side thereof. The reflecting portion 80142 and the moving portion 80141 are coupled to each other, and thus, move together. The reflecting portion 80142 is, for example, mirror surfaces, and has a function of generating reflected light depending on the incident light. When, for example, the movable optical member 8014 moves in the side-to-side direction, coordinates of the reflecting portion 80142 irradiated with the incident light can be changed to change a direction of the reflected light. Using the change in direction of the reflected light, on/off operation as a switch can be performed.

(Micromirror Device)

Next, a micromirror device according to the present invention is described.

The micromirror device according to the present invention includes a plurality of micromirrors and the piezoelectric actuators described above that are dynamically connected to the micromirrors, respectively.

Figure 10:
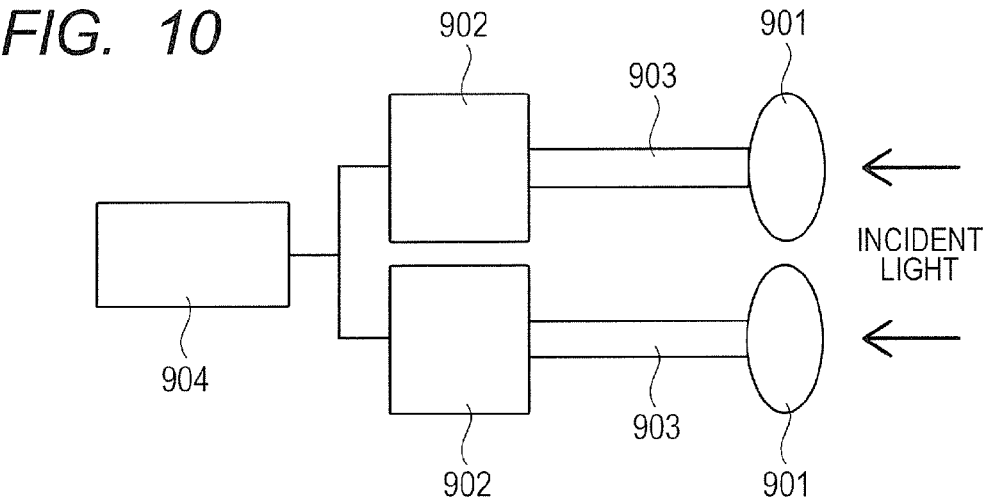
FIG. 10 is a schematic view for illustrating a configuration of a micromirror device according to an embodiment of the present invention.

FIG. 10 is a schematic view for illustrating a configuration of the micromirror device according to the present invention. The numbers, shapes, and arrangements of members are not limited to those illustrated in FIG. 10. In the micromirror device according to the present invention illustrated in FIG. 10, under instruction from a control portion 904, respective piezoelectric actuators 902 are deformed due to piezoelectric effec, directions and magnitudes of the deformation are adjusted by a piezoelectric strain transfer unit 903, and, as a result of those operations, micromirrors 901 are moved or rotated. The function described above enables reflection of light incident on the micromirrors in an arbitrary direction.

(Ultrasonic Wave Probe)

Next, an ultrasonic wave probe according to the present invention is described.

The ultrasonic wave probe according to the present invention includes the piezoelectric actuator described above, and has a function of oscillating an ultrasonic wave and a function of receiving a reflected wave.

Figure 11A:
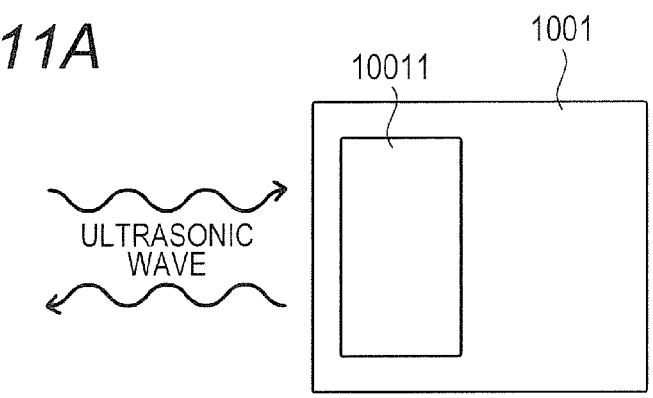
FIG. 11A and FIG. 11B are schematic views for illustrating configurations of an ultrasonic wave probe and an ultrasonograph according to embodiments, respectively, of the present invention.

FIG. 11A is a schematic view for illustrating a configuration of the ultrasonic wave probe according to the present invention. The numbers, shapes, and arrangements of members are not limited to those illustrated in FIG. 11A. An ultrasonic wave probe 1001 according to the present invention illustrated in FIG. 11A includes therein a piezoelectric actuator 10011, and an ultrasonic wave produced due to inverse piezoelectric effect of the piezoelectric actuator 10011 is oscillated (sent) toward a subject.

Wavy arrows in FIG. 11A schematically indicate ultrasonic wave propagation, and are not members of the ultrasonic wave probe 1001. The ultrasonic wave is reflected by internal tissue of the subject and returns toward the ultrasonic wave probe as ultrasonic echoes. Through conversion of vibrations caused by the ultrasonic echoes into electrical signals by the piezoelectric actuator 10011, information on the internal tissue of the subject can be obtained.

The piezoelectric actuator 10011 in charge of oscillation and reception of an ultrasonic wave may be a plurality of piezoelectric actuators, and one of the plurality of piezoelectric actuators may be a unit other than a piezoelectric actuator used in place thereof.

(Ultrasonograph)

Next, an ultrasonograph according to the present invention is described.

The ultrasonograph according to the present invention includes, the ultrasonic wave probe, a signal processing unit, and an image generating unit.

Figure 11B:
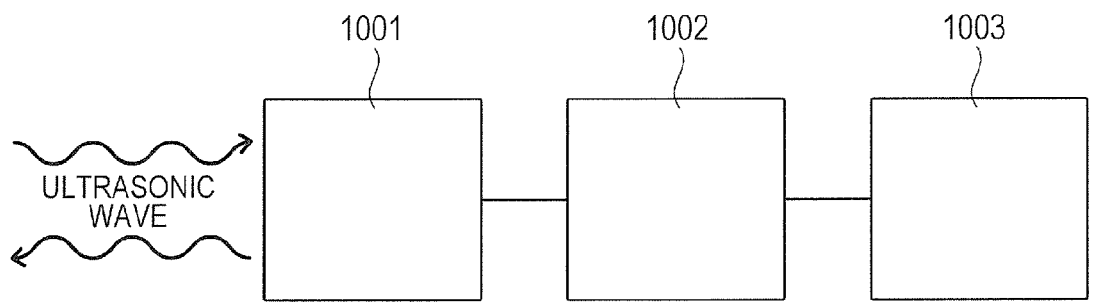

FIG. 11B is a schematic view for illustrating a configuration of the ultrasonograph according to the present invention. The order of connection of members is not limited to that illustrated in FIG. 11B. In the ultrasonograph according to the present invention illustrated in FIG. 11B, an electrical signal caused by a reflected wave received by the ultrasonic wave probe 1001 is subjected to data conversion and data accumulation in a signal processing unit 1002, and conversion into image information is made in an image forming unit 1003. The ultrasonograph also has a function of sending the image information to an external image display unit (display).

(Sound Component)

Next, a sound component according to the present invention is described.

A sound component according to the present invention includes the piezoelectric actuator and is configured to send or receive sound through driving of the piezoelectric actuator.

Figure 12:
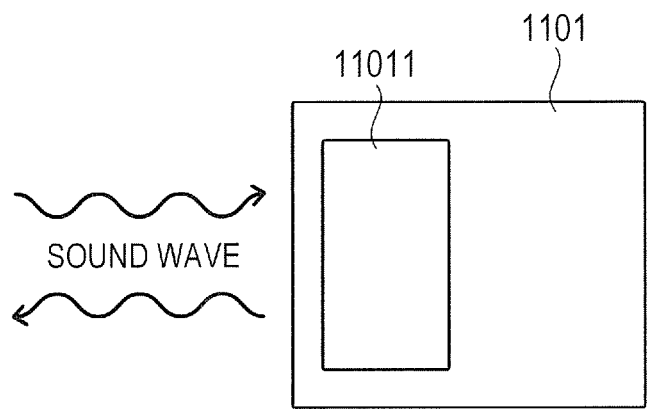
FIG. 12 is a schematic view for illustrating a configuration of a sound component according to an embodiment of the present invention.

FIG. 12 is a schematic view for illustrating a configuration of the sound component according to the present invention. The numbers, shapes, and arrangements of members are not limited to those illustrated in FIG. 12. A sound component 1101 according to the present invention illustrated in FIG. 12 includes therein a piezoelectric actuator 11011, and has a function of sending a sound wave produced due to inverse piezoelectric effect of the piezoelectric actuator 11011 and receiving a sound wave from the outside using positive piezoelectric effect. The sound component 1101 may include a diaphragm configured to amplify a sound wave. Wavy arrows in FIG. 12 schematically indicate sound wave propagation, and are not members of the sound component 1101. Exemplary sound components include a microphone, a speaker, and a buzzer.

(Angular Velocity Sensor)

Next, an angular velocity sensor according to the present invention is described.

The angular velocity sensor according to the present invention includes the piezoelectric element described above, and is configured to convert change in shape of the piezoelectric element into angular velocity information.

Figure 13:
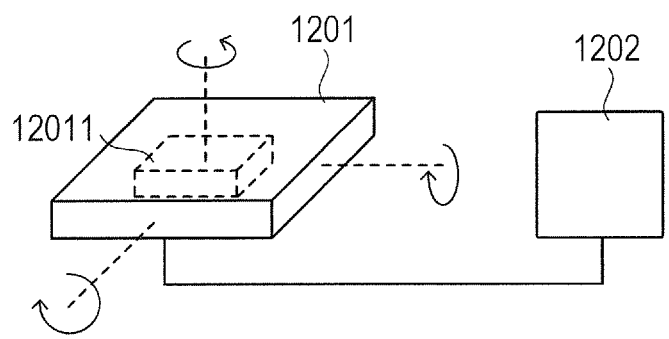
FIG. 13 is a schematic view for illustrating a configuration of an angular velocity sensor according to an embodiment of the present invention.

FIG. 13 is a schematic view for illustrating a configuration of the angular velocity sensor according to the present invention. The numbers, shapes, and arrangements of members are not limited to those illustrated in FIG. 13. An angular velocity sensor 1201 illustrated in FIG. 13 includes therein a piezoelectric element 12011, and a shape of the piezoelectric element 12011 is changed by a Coriolis force caused due to triaxial rotation of a body of the angular velocity sensor 1201. The change in shape of the piezoelectric element 12011 is converted into an electrical signal due to positive piezoelectric effect, and is converted into angular velocity information by a signal processing unit 1202 formed inside or outside the angular velocity sensor.

The angular velocity sensor 1201 may include a member other than the piezoelectric element 12011, and, as a configuration thereof, one known as a vibrating angular velocity sensor (gyro sensor) can be applied. Arrows and dotted lines in the vicinity thereof in FIG. 13 schematically indicate directions of the triaxial rotation, and are not members of the angular velocity sensor 1201.

(Vibration Power Generator)

Next, a vibration power generator according to the present invention is described.

The vibration power generator according to the present invention includes the piezoelectric element described above, and is configured to convert vibrational energy into electric energy.

Figure 14:
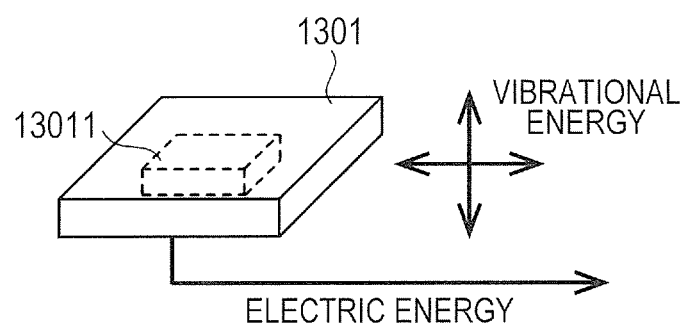
FIG. 14 is a schematic view for illustrating a configuration of a vibration power generator according to an embodiment of the present invention.

FIG. 14 is a schematic view for illustrating a configuration of the vibration power generator according to the present invention. The numbers, shapes, and arrangements of members are not limited to those illustrated in FIG. 14. A vibration power generator 1301 according to the present invention illustrated in FIG. 14 includes therein a piezoelectric element 13011, and has a power generating function of converting vibrational energy from the outside into electric energy using positive piezoelectric effect in the piezoelectric element 13011. The vibration power generator 1301 may include a vibration receiving portion for adjusting a direction and a frequency of vibration from the outside.

(Surface Acoustic Wave Generator)

Next, a surface acoustic wave generator according to the present invention is described.

The surface acoustic wave generator according to the present invention includes the piezoelectric element according to the second embodiment of the present invention.

Figure 15B:
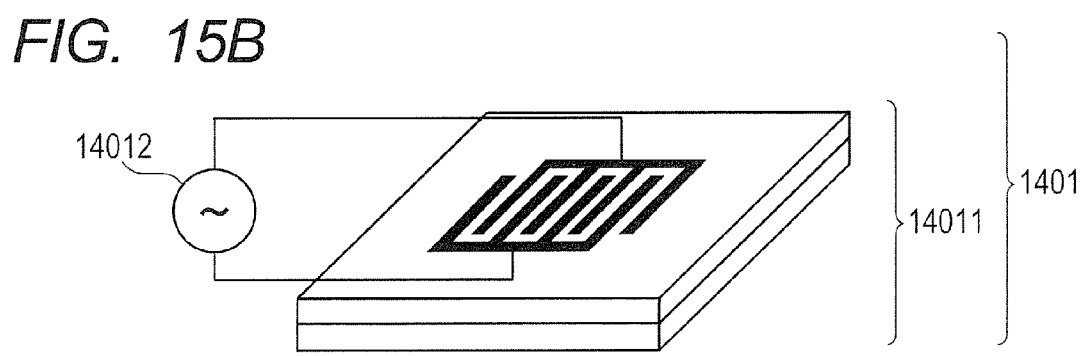

FIG. 15B is a schematic view for illustrating a configuration of the surface acoustic wave generator according to the present invention. The numbers, shapes, and arrangements of members are not limited to those illustrated in FIG. 15B. A surface acoustic wave generator 1401 according to the present invention illustrated in FIG. 15B includes therein a piezoelectric element 14011, and, through application of an alternating voltage by a power supply 14012, a surface acoustic wave is generated (excited) between an input side comb interdigital electrode (interdigital transducer: IDT) and an output side comb interdigital electrode. At this time, when a wavelength of the surface acoustic wave is a multiple of a cycle of arranging the IDTs, surface acoustic waves generated at the respective electrodes are in phase with each other, which improves a propagation state.

(Piezoelectric Shutter)

Next, a piezoelectric shutter according to the present invention is described.

The piezoelectric shutter according to the present invention includes the surface acoustic wave generator described above and a light-shielding component, and has a function of moving the light-shielding component by driving the surface acoustic wave generator.

Figure 15C:
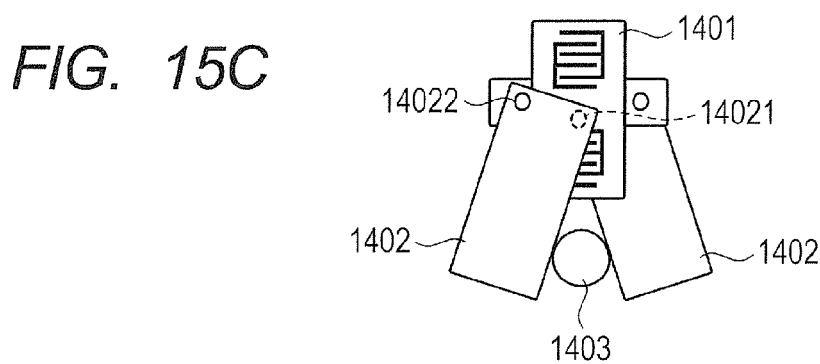
Figure 15D:
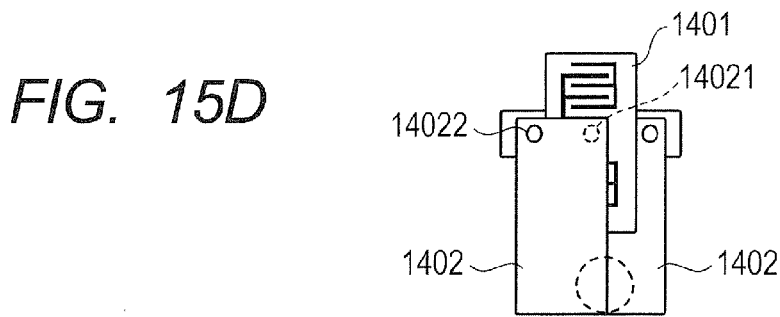

FIG. 15C and FIG. 15D are schematic views for illustrating a configuration of the piezoelectric shutter according to the present invention. The numbers, shapes, and arrangements of members are not limited to those illustrated in FIG. 15C and FIG. 15D.

The piezoelectric shutter according to the present invention illustrated in FIG. 15C includes the surface acoustic wave generator 1401 having a piezoelectric film and an IDT on each surface thereof, and an opaque light-shielding component 1402. The opaque light-shielding component 1402 has a movable protruding portion 14021 as a protruding portion configured to be in friction-contact with both surfaces of the surface acoustic wave generator 1401, and a rotation axis portion 14022 that is mounted to a housing and thus cannot be moved, but is rotatable. A light receiving portion 1403 configured to detect light passing through the piezoelectric shutter is an external member arranged beyond the plane of the drawing sheet, and is not included in the piezoelectric shutter.

When an alternating voltage is applied to the surface acoustic wave generator 1401 under a state in which the light receiving portion 1403 is not covered with the light-shielding component 1402 (open location) as illustrated in FIG. 15C to generate a surface acoustic wave that moves the movable protruding portion 14021 toward a top side within the plane of the drawing sheet, the light-shielding component 1402 starts rotational movement about the rotation axis portion 14022, and then, the state is as illustrated in FIG. 15D (closed location). Change from the closed location to the open location can be similarly made through movement of the movable protruding portion 14021 downward.

(Other Uses)

The piezoelectric element and the piezoelectric actuator according to the present invention can be applied to, other than the uses described above, overall piezoelectric devices employing a piezoelectric function. Exemplary uses include various kinds of piezoelectric sensors, ferroelectric memories, frequency filters, and piezoelectric oscillators. The piezoelectric element according to the present invention is not limited to the embodiments described above, and can be mounted on various electronic apparatus. With a member forming the electronic apparatus and a piezoelectric element formed in relation to the member, an electronic apparatus having excellent properties can be provided.

Now, the present invention is described more specifically by way of examples. However, the present invention is not limited by the following examples.

The piezoelectric element of the present invention was manufactured as described below.

(Manufacture Example of First Raw Material Liquid)

A plurality of first raw material liquids containing Ba, Ti, Zr, and Sn at various composition ratios were prepared. Some of the prepared first raw material liquids did not contain Sn. In preparing the raw material liquids, ones in which alkoxides of the respective metals were mixed and dispersed in an organic solvent were used.

As a Ba material, $Ba(OC_2H_5)_2$ was used. As a Ca material, $Ca(OC_2H_5)_2$ was used. As a Ti material, $Ti(OC_2H_5)_4$ was used. As a Zr material, $Zr(O-n-C_4H_9)_4$ was used. As a Sn material, $Sn(O-i-C_3H_7)_4$ was used.

As the organic solvent, 1-methoxy-2-propanol was used, but when a general organic solvent, such as diethylene glycol monoethyl ether, acetylacetone, ethanol, isopropyl alcohol, n-butanol, ethylene glycol, propylene glycol, n-butyl acetate, xylene, toluene, or octane, was used for the purposes of enhancing stability and adjusting viscosity of the raw material liquid, a similar result was obtained. As a stabilizer, 1,8-diazabicyclo[5.4.0]-7-undecene was used. Concentrations of the metal components in the raw material liquids were adapted to be from 20 mass % to 25 mass % based on metal oxides.

Content ratios of Ba, Ca, Ti, Zr, and Sn components in the raw material liquids in preparation were set such that x' was from 0.09 to 0.30, y' was from 0.025 to 0.085, and z' was from 0 (not contained in preparation) to 0.02, assuming the general formula (2) of $(Ba_{1-x'}Ca_{x'})(Ti_{1-y'-z'}Zr_{y'}Sn_{z'})O_3$ of the metal oxide after the firing. Values of x', y', and z' in the first raw material liquids used in respective Examples are shown in Table 1.

The total contents of Mn and Bi in the respective raw material liquids after being prepared were less than 100 ppm except for the liquid used in Example 17. In the first raw material liquid used in Example 17, equal amounts of $Bi(O-i-C_3H_7)_3$ and $Mn(O-i-C_3H_7)_2$ were added such that the total content of Mn and Bi was 700 ppm.

(Manufacture Example of Second Raw Material Liquid)

A plurality of second raw material liquids containing Ba, Ca, Ti, Zr, Sn, Mn, and Bi at various composition ratios were prepared. Some of the prepared second raw material liquids did not contain Mn, Sn, or Bi. In preparing raw material liquids, ones in which alkoxides of the respective metals were mixed and dispersed in an organic solvent were used. Manufacture was conducted such that the materials of Ba, Ca, Ti, Zr, and Sn, the organic solvent, the stabilizer, and the concentration of the sum of the metal components were the same as those in the first raw material liquids.

As a Bi material, $Bi(O-i-C_3H_7)_3$ was used. As a Mn material, $Mn(O-i-C_3H_7)_2$ was used.

Content ratios of Ba, Ca, Ti, Zr, and Sn components in the raw material liquids in preparation were set such that x was from 0.09 to 0.30, y was from 0.025 to 0.085, and z was from 0 (not contained in preparation) to 0.02, assuming the general formula (1) of $(Ba_{1-x}Ca_x)(Ti_{1-y-z}Zr_ySn_z)O_3$ of the metal oxide after the firing. Values of x, y, and z in the second raw material liquids used in respective Examples are shown in Table 1.

Content ratios of Mn and Bi components in the raw material liquids in preparation were set such that the concentration of single-component Mn was 0 moles or more and 0.012 moles or less, the concentration of single-component Bi was 0 moles or more and 0.008 moles or less, and the concentration of the sum of Mn and Bi was 0.002 moles or more and 0.02 moles or less when the molar amount of the sum of Ti and Zr was 1 mole. Mn concentrations and Bi concentrations in the second raw material liquids used in respective Examples are shown in Table 1. In Table 2, the Mn concentrations and the Bi concentrations are indicated as dimensionless quantities of mol/mol as molar amount ratios of Mn or Bi with respect to the molar amount of the sum of Ti and Zr.

(Manufacture Example of Third Raw Material Liquid)

Preparation was made similarly to that of the manufacture example of the first raw material liquid. Abundance ratios of the respective components are as shown in Table 1.

(Piezoelectric Element)

EXAMPLE 1

As the first electrode, a platinum electrode having a thickness of 400 nm was formed on a commercially available silicon substrate by DC sputtering. As an adhering layer, a titanium oxide film having a thickness of 30 nm was formed between the first electrode and the silicon substrate. Qualitative composition analysis of the first electrode was conducted using an electron probe microanalyzer (EPMA), and it was found that only Pt and Ti were detected, Mn and Bi were not detected, and the total content of Mn and Bi was less than 50 ppm.

Then, the piezoelectric film lower layer was formed by CSD on the first electrode using the first raw material liquid. Specifically, the first raw material liquid in which the respective metals were prepared so as to correspond to $x'=0.17$, $y'=0.06$, and $z'=0.01$ in the general formula (2) of $(Ba_{1-x'}Ca_{x'})(Ti_{1-y'-z'}Zr_{y'}Sn_{z'})O_3$ (see Table 1) was spin coated (3,000 rpm) on the first electrode at room temperature. After the applied film was dried on a hot plate (250° C. to 400° C.), the substrate was placed in an electric furnace at 600° C. for 15 minutes to preliminarily fire the applied film. Through repetition of the steps of application, drying, and preliminarily firing three times, the piezoelectric film lower layer having a thickness of about 500 nm was obtained.

Then, the piezoelectric film intermediate layer was formed by CSD on the piezoelectric film lower layer using the second raw material liquid.

Specifically, the second raw material liquid was used in which the respective metals were prepared so as to correspond to $x=0.17$, $y=0.06$, and $z=0.01$ in the general formula (1) of $(Ba_{1-x}Ca_x)(Ti_{1-y-z}Zr_ySn_z)O_3$ and Mn and Bi were prepared such that the Mn concentration was 0.006 moles and the Bi concentration was 0.002 moles when the molar amount of the sum of Ti and Zr was 1 mole (see Table 1).

The second raw material liquid was spin coated (2,000 rpm) on the piezoelectric film lower layer at room temperature. After the applied film was dried on a hot plate (250° C. to 400° C.), the substrate was placed in an electric furnace at 600° C. for 15 minutes to preliminarily fire the applied film. Through repetition of the steps of application, drying, and preliminarily firing seven times, the piezoelectric film intermediate layer having a thickness of about 2,000 nm was obtained.

Then, the piezoelectric film upper layer was formed by CSD on the piezoelectric film intermediate layer using the third raw material liquid.

Specifically, the third raw material liquid having the same composition as that of the first raw material liquid (see Table 1) was spin coated (3,000 rpm) on the piezoelectric film intermediate layer at room temperature. After the applied film was dried on a hot plate (250° C. to 400° C.), the substrate was placed in an electric furnace at 600° C. for 15 minutes to preliminarily fire the applied film. Through repetition of the steps of application, drying, and preliminarily firing three times, the piezoelectric film upper layer having a thickness of about 500 nm was obtained. At the end of those steps, as main firing, the substrate with the film formed thereon was placed in an electric furnace at 750° C. for two hours to obtain a crystallized piezoelectric film.

Then, a platinum electrode having a thickness of 400 nm was formed as the second electrode on the piezoelectric film by DC sputtering. As an adhering layer, a titanium oxide film having a thickness of 30 nm was formed between the second electrode and the piezoelectric film.

In this way, the piezoelectric element according to the present invention was obtained.

The piezoelectric element was cut and a section thereof was observed under a microscope. It was confirmed that the silicon substrate, the first electrode, the piezoelectric film, and the second electrode were laminated in this order, and that the first electrode and the second electrode sandwiched the piezoelectric film on the substrate. Further, the portion of the piezoelectric film sandwiched between the first electrode and the second electrode was substantially planar, and the thickness thereof measured using a function of the microscope was about 3,000 nm. The first and second electrodes had a thickness of about 400 nm. Composition analysis of an interface portion between the first electrode and the substrate was conducted using a transmission electron microscope (TEM) and electron energy loss spectroscopy (EELS) in combination, and it was confirmed that an adhering component of a Ti metal component existed. A section of the piezoelectric film portion was observed under a transmission electron microscope, and it was confirmed that, from a contrast in electron diffraction, almost the entire region of the section had an aggregate structure formed of grains each having a columnar structure. A grain size at the surface of the film as an average equivalent circle diameter was 1,800 nm.

Composition analysis of the cut section of the piezoelectric film portion of the piezoelectric element was conducted using TEM and EELS in combination, and composition analysis of the region in a layer form at a thickness of 100 nm adjacent to the first electrode was conducted. As a result, it was found that the composition of the region of the piezoelectric film adjacent to the first electrode was expressed by the chemical formula $(Ba_{0.83}Ca_{0.17})(Ti_{0.93}Zr_{0.06}Sn_{0.01})O_3$. Mn and Bi were hardly detected, and it was determined that the total content of Mn and Bi was 100 ppm or less. In other words, $S_{bou}$ was estimated to be as small as 0.0001 at the maximum. In this example, the Mn concentration and the Bi concentration below a detection limit were regarded as zero.

Composition analysis of the region adjacent to the second electrode was conducted at the same thickness, and, similarly, it was found that the composition was able to be expressed by the chemical formula $(Ba_{0.83}Ca_{0.17})(Ti_{0.93}Zr_{0.06}Sn_{0.01})O_3$. Mn and Bi were hardly detected, and the total content of Mn and Bi was less than 100 ppm.

In the EELS composition analysis of the first electrode portion and the second electrode portion, only Pt and Ti were detected and Mn and Bi were not detected, and it was found that the total content of Mn and Bi in the electrode portions was less than 50 ppm.

X-ray diffraction measurement of the piezoelectric film portion of the piezoelectric element was conducted. In the entire temperature range of from −30° C. to 50° C., only a peak corresponding to the perovskite structure of a non-oriented tetragonal crystal was observed. A lattice constant of a tetragonal crystal structure converted from the peak was compared with a known lattice constant of bulk ceramics having the same composition, and it was found that the piezoelectric film of the piezoelectric element of Example had internal residual stress in a tensile direction due to restraint by the substrate.

The second electrode of the piezoelectric element was removed by polishing processing, and an average composition of the entire piezoelectric film was analyzed by XRF. It was found that a principal component was a metal oxide that was able to be expressed by the chemical formula $(Ba_{0.83}Ca_{0.17})(Ti_{0.93}Zr_{0.06}Sn_{0.01})O_3$. Further, it was found that 0.004 moles of Mn element and 0.001 moles of Bi element were contained for 1 mole of the metal oxide. Therefore, $S_{ave}$ of this piezoelectric element was 0.005.

This result was combined with the result of the local composition analysis of the regions adjacent to the electrodes, to thereby find that $S_{bou}/S_{ave}$ was in the range of from 0% to 2%. Further, all of $|x-x'|$, $|y-y'|$, and $|z-z'|$ were zero within the measurement accuracy. Therefore, $S_{bou}/S_{ave}=0$.

In this example, $S_{bou}$ was calculated when the region adjacent to the first electrode had a thickness of 100 nm, but, even when $S_{bou}$ was calculated with the thickness of the region adjacent to the electrode being changed from 5 nm to 150 nm, in any one of those cases, $S_{bou}$ was smaller than $S_{ave}$, and $S_{bou}/S_{ave}$ was in the range of from 0% to 2%.

When the composition distribution was mapped with regard to the surface of the piezoelectric film using EPMA, it was confirmed that, for any one of the metal elements, wide variations in composition in the film surface direction were not observed, and the variations were within 0.001 moles.

The piezoelectric element was placed in an environmental test chamber in which a temperature was controlled to be from −30° C. to 200° C., the first electrode and the second electrode of the piezoelectric element were connected to an impedance analyzer (4194A manufactured by Agilent Technologies), and capacitances and dielectric losses at the respective temperatures were measured. An applied voltage was 0.05 V, and values when the frequency was 1 kHz were measured. As a result, it was found that the dielectric loss of the piezoelectric element of Example 1 was 0.50% (0.0050) at room temperature (25° C.) and 0.60% (0.0060) at the maximum in the range of from −30° C. to 50° C. urther, the Curie temperature of the piezoelectric film determined from the maximum of the capacitance was 150° C.

Next, for the purpose of measuring a piezoelectric constant $d_{31}$, the piezoelectric element according to the present invention was cut into a strip shape having a length of 15 mm and a width of 2.5 mm and was used as a cantilever. An end portion of the cantilever in a longitudinal direction was fixed, and an alternating voltage was applied to the piezoelectric element. An amount of displacement of vertically reciprocating an end portion of the piezoelectric element on a side opposite to the fixed end portion was measured with a laser Doppler displacement gauge, which was able to be converted into the piezoelectric constant $d_{31}$ using information such as a shape and a Young's modulus of the cantilever.

An alternating voltage of ±10 V at 10 kHz was applied across the electrodes of the cantilever at room temperature, and a drive test was conducted for 720 hours and the constant $d_{31}$ was measured during the test. An absolute value $|d_{31}|$ of the initial constant $d_{31}$ was 95 pm/V, and the absolute value $|d_{31}|$ after the drive test was repeated about $2.6 \times 10^{10}$ times was 94 pm/V, and thus, a retention rate of the constant $d_{31}$ was 99%.

EXAMPLES 2 TO 24

A piezoelectric element according to the present invention was obtained in a manufacturing method similar to that of Example 1. However, component ratios of the first raw material liquid, the second raw material liquid, and the third raw material liquid were changed as shown in Table 1. Further, kinds of the substrate and the first electrode, the number of times of applying the raw material liquids, the highest temperatures in firing, and kinds of the second electrodes were changed as shown in Table 2.

"100 oriented monocrystal" of Example 18 in Table 2 refers to a MgO monocrystalline substrate that was cut out such that a film forming surface thereof was a (100) plane. Similarly, in Example 19, a MgO monocrystalline substrate in which a film forming surface was a (110) plane was used, and, in Example 20, a MgO monocrystalline substrate in which a film forming surface was a (111) plane was used. In Example 15, a gold thin film formed by DC sputtering was used as the first electrode and the second electrode.

Similarly to the case of Example 1, the piezoelectric element was cut and a section thereof was observed under a microscope. It was confirmed that the silicon substrate, the first electrode, the piezoelectric film, and the second electrode were laminated in this order, and that the first electrode and the second electrode sandwiched the piezoelectric film on the substrate. Thicknesses measured using the function of the microscope are shown in Table 3. The first and second electrodes had a thickness of about 400 nm in any one of Examples. Composition analysis of the interface portion between the first electrode and the substrate was conducted using a transmission electron microscope (TEM) and electron energy loss spectroscopy (EELS) in combination, and it was confirmed that an adhering component of a Ti metal component existed. A section of the piezoelectric film portion was observed under a transmission electron microscope, and it was confirmed that, from a contrast in electron diffraction, almost the entire region of the section had an aggregate structure formed of grains each having a columnar structure. A grain size at the surface of the film as an average equivalent circle diameter was in a range of from 300 nm to 5,000 nm.

Similarly to the case of Example 1, the composition of the region in a layer form at a thickness of 100 nm adjacent to the first electrode and an average composition of the entire piezoelectric film were specified, and $S_{ave}$ and $S_{bou}$ were calculated. Results are shown in Table 3.

Similarly to the case of Example 1, the dielectric losses, the initial constants $d_{31}$, and the constants $d_{31}$ after the drive test was repeated about $2.6 \times 10^{10}$ times of the piezoelectric elements according to the present invention were determined, and results are shown in Table 4. The constants $d_{31}$ in Table 4 are shown as absolute values thereof. The Curie temperature of the piezoelectric elements of Examples was 130° C. at the lowest and 195° C. at the highest.

COMPARATIVE EXAMPLE 1

A piezoelectric element for comparison was manufactured similarly to the case of Example 1 except that a raw material liquid in which the respective metals were prepared so as to correspond to x=0.17, y=0.06, and z=0.01 in the general formula (1) of $(Ba_{1-x}Ca_x)(Ti_{1-y-z}Zr_ySn_z)O_3$ and Mn and Bi were prepared such that the Mn concentration was 0.004 moles and the Bi concentration was 0.001 moles when the molar amount of the sum of Ti and Zr was 1 mole was used as the first, second, and third raw material liquids.

As a result of composition analysis of the entire piezoelectric film and local composition analysis, $S_{bou}/S_{ave}$ in the vicinity of the first electrode was about 1.02. Further, in the first electrode portion, about 800 ppm of Mn and about 200 ppm of Bi were detected.

A drive test was conducted similarly to the case of Example 1. With regard to the initial constant $d_{31}$, $|d_{31}|$ was 105 pm/V, which was larger than that of Example 1. However, $|d_{31}|$ after the drive test was repeated about $2.6 \times 10^{10}$ times was 55 pm/V, and thus, the retention rate of the constant $d_{31}$ was 52%. Other physical properties were as shown in Table 3 and Table 4.

COMPARATIVE EXAMPLES 2 TO 8

A piezoelectric element for comparison was obtained in a manufacturing method similar to that of Comparative Example 1. However, component ratios of the first raw material liquid, the second raw material liquid, and the third raw material liquid were changed as shown in Table 1.

Similarly to the case of Example 1, the piezoelectric element was cut and a section thereof was observed under a microscope. It was confirmed that the silicon substrate, the first electrode, the piezoelectric film, and the second electrode were laminated in this order, and that the first electrode and the second electrode sandwiched the piezoelectric film on the substrate. Thicknesses measured using the function of the microscope are shown in Table 3. The first and second electrodes had a thickness of about 400 nm in any one of Examples. Composition analysis of the interface portion between the first electrode and the substrate was conducted using a transmission electron microscope (TEM) and electron energy loss spectroscopy (EELS) in combination, and it was confirmed that an adhering component of a Ti metal component existed.

Similarly to the case of Example 1, the composition of the region in a layer form at a thickness of 100 nm adjacent to the first electrode and an average composition of the entire piezoelectric film were specified, and $S_{ave}$ and $S_{bou}$ were calculated. Results are shown in Table 3.

Similarly to the case of Example 1, the dielectric losses, the initial constants $d_{31}$, and the constants $d_{31}$ after the drive test was repeated about $2.6 \times 10^{10}$ times of the piezoelectric elements for comparison were determined, and the results are shown in Table 4. The constants $d_{31}$ in Table 4 are shown as absolute values thereof.

With regard to the piezoelectric elements of Comparative Example 4 and Comparative Example 8, the absolute values of the initial constants $d_{31}$ were as small as less than 60 pm/V, and thus, the two were determined to be inferior in practicality and the drive test therefor was not conducted.

TABLE 1

| | First raw material liquid | | | | Second raw material liquid | | Third raw material liquid | | | | |
|---|---|---|---|---|---|---|---|---|---|---|---|
| | Mn + Bi concentration | x' | y' | z' | Mn concentration (mol/mol) | Bi concentration (mol/mol) | x | y | z | Mn + Bi concentration | x' | y' | z' |
| Example 1 | Less than 100 ppm | 0.170 | 0.060 | 0.010 | 0.0060 | 0.0020 | 0.170 | 0.060 | 0.010 | Less than 100 ppm | 0.170 | 0.060 | 0.010 |
| Example 2 | Less than 100 ppm | 0.170 | 0.060 | 0.010 | 0.0030 | 0 | 0.170 | 0.060 | 0.010 | Less than 100 ppm | 0.170 | 0.060 | 0.010 |
| Example 3 | Less than 100 ppm | 0.170 | 0.060 | 0.010 | 0 | 0.0030 | 0.170 | 0.060 | 0.010 | Less than 100 ppm | 0.170 | 0.060 | 0.010 |
| Example 4 | Less than 100 ppm | 0.170 | 0.060 | 0.010 | 0.0060 | 0.0060 | 0.170 | 0.060 | 0.010 | Less than 100 ppm | 0.170 | 0.060 | 0.010 |
| Example 5 | Less than 100 ppm | 0.170 | 0.060 | 0.010 | 0.0100 | 0.0060 | 0.170 | 0.060 | 0.010 | Less than 100 ppm | 0.170 | 0.060 | 0.010 |
| Example 6 | Less than 100 ppm | 0.170 | 0.060 | 0.010 | 0.0120 | 0.0060 | 0.170 | 0.060 | 0.010 | Less than 100 ppm | 0.170 | 0.060 | 0.010 |
| Example 7 | Less than 100 ppm | 0.170 | 0.025 | 0.010 | 0.0060 | 0.0020 | 0.170 | 0.025 | 0.010 | Less than 100 ppm | 0.170 | 0.025 | 0.010 |
| Example 8 | Less than 100 ppm | 0.170 | 0.085 | 0.010 | 0.0060 | 0.0020 | 0.170 | 0.085 | 0.010 | Less than 100 ppm | 0.170 | 0.085 | 0.010 |
| Example 9 | Less than 100 ppm | 0.170 | 0.060 | 0 | 0.0060 | 0.0020 | 0.170 | 0.060 | 0 | Less than 100 ppm | 0.170 | 0.060 | 0 |
| Example 10 | Less than 100 ppm | 0.170 | 0.060 | 0.020 | 0.0060 | 0.0020 | 0.170 | 0.060 | 0.020 | Less than 100 ppm | 0.170 | 0.060 | 0.020 |
| Example 11 | Less than 100 ppm | 0.090 | 0.060 | 0.010 | 0.0060 | 0.0020 | 0.090 | 0.060 | 0.010 | Less than 100 ppm | 0.090 | 0.060 | 0.010 |
| Example 12 | Less than 100 ppm | 0.120 | 0.060 | 0.010 | 0.0060 | 0.0020 | 0.120 | 0.060 | 0.010 | Less than 100 ppm | 0.120 | 0.060 | 0.010 |
| Example 13 | Less than 100 ppm | 0.200 | 0.060 | 0.010 | 0.0060 | 0.0020 | 0.200 | 0.060 | 0.010 | Less than 100 ppm | 0.200 | 0.060 | 0.010 |
| Example 14 | Less than 100 ppm | 0.300 | 0.060 | 0.010 | 0.0060 | 0.0020 | 0.300 | 0.060 | 0.010 | Less than 100 ppm | 0.300 | 0.060 | 0.010 |
| Example 15 | Less than 100 ppm | 0.170 | 0.060 | 0.010 | 0.0060 | 0.0020 | 0.170 | 0.060 | 0.010 | Less than 100 ppm | 0.17 | 0.060 | 0.010 |
| Example 16 | Less than 100 ppm | 0.190 | 0.050 | 0 | 0.0060 | 0.0020 | 0.160 | 0.065 | 0.015 | Less than 100 ppm | 0.190 | 0.050 | 0 |
| Example 17 | 700 ppm | 0.170 | 0.060 | 0.010 | 0.0060 | 0.0020 | 0.170 | 0.060 | 0.010 | 700 ppm | 0.170 | 0.060 | 0.010 |
| Example 18 | Less than 100 ppm | 0.170 | 0.060 | 0.010 | 0.0060 | 0.0020 | 0.170 | 0.060 | 0.010 | Less than 100 ppm | 0.170 | 0.060 | 0.010 |
| Example 19 | Less than 100 ppm | 0.170 | 0.060 | 0.010 | 0.0060 | 0.0020 | 0.170 | 0.060 | 0.010 | Less than 100 ppm | 0.170 | 0.060 | 0.010 |
| Example 20 | Less than 100 ppm | 0.170 | 0.060 | 0.010 | 0.0060 | 0.0020 | 0.170 | 0.060 | 0.010 | Less than 100 ppm | 0.170 | 0.060 | 0.010 |
| Comparative Example 1 | 0.005 moles | 0.170 | 0.060 | 0.010 | 0.0040 | 0.001 | 0.170 | 0.060 | 0.010 | 0.005 moles | 0.170 | 0.060 | 0.010 |
| Comparative Example 2 | Less than 100 ppm | 0.170 | 0.060 | 0.010 | 0.0210 | 0 | 0.170 | 0.060 | 0.010 | Less than 100 ppm | 0.170 | 0.060 | 0.010 |
| Comparative Example 3 | Less than 100 ppm | 0.170 | 0.060 | 0.010 | 0 | 0.0210 | 0.170 | 0.060 | 0.010 | Less than 100 ppm | 0.170 | 0.060 | 0.010 |
| Comparative Example 4 | Less than 100 ppm | 0.170 | 0.010 | 0.010 | 0.0060 | 0.0020 | 0.170 | 0.010 | 0.010 | Less than 100 ppm | 0.170 | 0.010 | 0.010 |
| Comparative Example 5 | Less than 100 ppm | 0.170 | 0.090 | 0.010 | 0.0060 | 0.0020 | 0.170 | 0.090 | 0.010 | Less than 100 ppm | 0.170 | 0.090 | 0.010 |
| Comparative Example 6 | Less than 100 ppm | 0.170 | 0.060 | 0.030 | 0.0060 | 0.0020 | 0.170 | 0.060 | 0.030 | Less than 100 ppm | 0.170 | 0.060 | 0.030 |
| Comparative Example 7 | Less than 100 ppm | 0 | 0.060 | 0.010 | 0.0060 | 0.0020 | 0.000 | 0.060 | 0.010 | Less than 100 ppm | 0.000 | 0.060 | 0.010 |
| Comparative Example 8 | Less than 100 ppm | 0.350 | 0.060 | 0.010 | 0.0060 | 0.0020 | 0.350 | 0.060 | 0.010 | Less than 100 ppm | 0.350 | 0.060 | 0.010 |

TABLE 2

| | Substrate | Adhering layer | First electrode | Number of times of applying first raw material liquid | First raw material liquid firing temperature | Number of times of applying second raw material liquid | Second raw material liquid firing temperature | Number of times of applying third raw material liquid | Third raw material liquid firing temperature | Second electrode |
|---|---|---|---|---|---|---|---|---|---|---|
| Example 1 | Silicon | Ti | Pt | Three times | 600° C. | Seven times | 600° C. | Three times | 750° C. | Pt |
| Example 2 | Silicon | Ti | Pt | Three times | 600° C. | Seven times | 600° C. | Three times | 750° C. | Pt |
| Example 3 | Silicon | Ti | Pt | Three times | 600° C. | Seven times | 600° C. | Three times | 750° C. | Pt |

TABLE 2-continued

| | Substrate | Adhering layer | First electrode | Number of times of applying first raw material liquid | First raw material liquid firing temperature | Number of times of applying second raw material liquid | Second raw material liquid firing temperature | Number of times of applying third raw material liquid | Third raw material liquid firing temperature | Second electrode |
|---|---|---|---|---|---|---|---|---|---|---|
| Example 4 | Silicon | Ti | Pt | Three times | 620° C. | Seven times | 620° C. | Three times | 780° C. | Pt |
| Example 5 | Silicon | Ti | Pt | Three times | 650° C. | Seven times | 650° C. | Three times | 780° C. | Pt |
| Example 6 | Silicon | Ti | Pt | One Time | 650° C. | Seven times | 650° C. | One time | 800° C. | Pt |
| Example 7 | Silicon | Ti | Pt | Three times | 600° C. | Seven times | 600° C. | Three times | 750° C. | Pt |
| Example 8 | Silicon | Ti | Pt | Three times | 600° C. | Seven times | 600° C. | Three times | 750° C. | Pt |
| Example 9 | Silicon | Ti | Pt | Three times | 600° C. | Seven times | 600° C. | Three times | 750° C. | Pt |
| Example 10 | Silicon | Ti | Pt | Three times | 600° C. | Seven times | 600° C. | Three times | 750° C. | Pt |
| Example 11 | Silicon | Ti | Pt | Three times | 600° C. | Seven times | 600° C. | Three times | 750° C. | Pt |
| Example 12 | Silicon | Ti | Pt | Three times | 600° C. | Seven times | 600° C. | Three times | 750° C. | Pt |
| Example 13 | Silicon | Ti | Pt | Three times | 600° C. | Seven times | 600° C. | Three times | 750° C. | Pt |
| Example 14 | Silicon | Ti | Pt | Three times | 600° C. | Seven times | 600° C. | Three times | 750° C. | Pt |
| Example 15 | Silicon | Ti | Au | Two times | 550° C. | Three times | 550° C. | Two times | 750° C. | Au |
| Example 16 | Silicon | Ti | Pt | Three times | 600° C. | Seven times | 600° C. | Three times | 750° C. | Pt |
| Example 17 | Silicon | Ti | Pt | Five times | 600° C. | Seven times | 600° C. | Five times | 750° C. | Pt |
| Example 18 | 100 oriented monocrystal | Ti | Pt | Three times | 600° C. | Seven times | 600° C. | Three times | 750° C. | Pt |
| Example 19 | 110 oriented monocrystal | Ti | Pt | Three times | 600° C. | Seven times | 600° C. | Three times | 750° C. | Pt |
| Example 20 | 111 oriented monocrystal | Ti | Pt | Three times | 600° C. | Seven times | 600° C. | Three times | 750° C. | Pt |
| Comparative Example 1 | Silicon | Ti | Pt | Three times | 600° C. | Seven times | 600° C. | Three times | 750° C. | Pt |
| Comparative Example 2 | Silicon | Ti | Pt | Three times | 600° C. | Seven times | 600° C. | Three times | 750° C. | Pt |
| Comparative Example 3 | Silicon | Ti | Pt | Three times | 600° C. | Seven times | 600° C. | Three times | 750° C. | Pt |
| Comparative Example 4 | Silicon | Ti | Pt | Three times | 600° C. | Seven times | 600° C. | Three times | 750° C. | Pt |
| Comparative Example 5 | Silicon | Ti | Pt | Three times | 600° C. | Seven times | 600° C. | Three times | 750° C. | Pt |
| Comparative Example 6 | Silicon | Ti | Pt | Three times | 600° C. | Seven times | 600° C. | Three times | 750° C. | Pt |
| Comparative Example 7 | Silicon | Ti | Pt | Three times | 600° C. | Seven times | 600° C. | Three times | 750° C. | Pt |
| Comparative Example 8 | Silicon | Ti | Pt | Three times | 600° C. | Seven times | 600° C. | Three times | 750° C. | Pt |

TABLE 3

| | Piezoelectric film thickness [nm] | Average in entire piezoelectric film | | | Region in layer form at thickness of 100 nm adjacent to first electrode | | | Average in entire piezoelectric film | |
|---|---|---|---|---|---|---|---|---|---|
| | | Ca x | Zr y | Sn z | Ca x' | Zr y' | Sn z' | $S_{ave}$ (mol/mol) | Mn concentration (mol/mol) |
| Example 1 | 3,000 | 0.170 | 0.060 | 0.010 | 0.170 | 0.060 | 0.010 | 0.0050 | 0.0040 |
| Example 2 | 3,000 | 0.170 | 0.060 | 0.010 | 0.170 | 0.060 | 0.010 | 0.0020 | 0.0020 |
| Example 3 | 3,000 | 0.170 | 0.060 | 0.010 | 0.170 | 0.060 | 0.010 | 0.0020 | 0 |
| Example 4 | 2,800 | 0.170 | 0.060 | 0.010 | 0.170 | 0.060 | 0.010 | 0.0100 | 0.0050 |
| Example 5 | 2,700 | 0.170 | 0.060 | 0.010 | 0.170 | 0.060 | 0.010 | 0.0130 | 0.0080 |
| Example 6 | 2,200 | 0.170 | 0.060 | 0.010 | 0.170 | 0.060 | 0.010 | 0.0150 | 0.0100 |
| Example 7 | 3,000 | 0.170 | 0.025 | 0.010 | 0.170 | 0.025 | 0.010 | 0.0050 | 0.0040 |
| Example 8 | 3,000 | 0.170 | 0.085 | 0.010 | 0.170 | 0.085 | 0.010 | 0.0050 | 0.0040 |
| Example 9 | 3,000 | 0.170 | 0.060 | 0 | 0.170 | 0.060 | 0 | 0.0050 | 0.0040 |
| Example 10 | 3,000 | 0.170 | 0.060 | 0.020 | 0.170 | 0.060 | 0.020 | 0.0050 | 0.0040 |
| Example 11 | 3,000 | 0.090 | 0.060 | 0.010 | 0.090 | 0.060 | 0.010 | 0.0050 | 0.0040 |
| Example 12 | 3,000 | 0.120 | 0.060 | 0.010 | 0.120 | 0.060 | 0.010 | 0.0050 | 0.0040 |
| Example 13 | 3,000 | 0.200 | 0.060 | 0.010 | 0.200 | 0.060 | 0.010 | 0.0050 | 0.0040 |
| Example 14 | 3,000 | 0.300 | 0.060 | 0.010 | 0.300 | 0.060 | 0.010 | 0.0050 | 0.0040 |
| Example 15 | 1,900 | 0.170 | 0.060 | 0.010 | 0.170 | 0.060 | 0.010 | 0.0045 | 0.0040 |
| Example 16 | 3,000 | 0.170 | 0.060 | 0.010 | 0.190 | 0.050 | 0 | 0.0050 | 0.0040 |
| Example 17 | 4,000 | 0.170 | 0.060 | 0.010 | 0.170 | 0.060 | 0.010 | 0.0035 | 0.0030 |
| Example 22 | 2,800 | 0.170 | 0.060 | 0.010 | 0.170 | 0.060 | 0.010 | 0.0050 | 0.0040 |
| Example 23 | 2,800 | 0.170 | 0.060 | 0.010 | 0.170 | 0.060 | 0.010 | 0.0050 | 0.0040 |
| Example 24 | 2,800 | 0.170 | 0.060 | 0.010 | 0.170 | 0.060 | 0.010 | 0.0050 | 0.0040 |
| Comparative | 3,000 | 0.170 | 0.060 | 0.010 | 0.170 | 0.060 | 0.010 | 0.0050 | 0.0040 |

TABLE 3-continued

| | | | | | | | | | |
|---|---|---|---|---|---|---|---|---|---|
| Example 1 | | | | | | | | | |
| Comparative Example 2 | 3,000 | 0.170 | 0.060 | 0.010 | 0.170 | 0.060 | 0.010 | 0.0200 | 0.0200 |
| Comparative Example 3 | 3,000 | 0.170 | 0.060 | 0.010 | 0.170 | 0.060 | 0.010 | 0.0200 | 0 |
| Comparative Example 4 | 3,000 | 0.170 | 0.010 | 0.010 | 0.170 | 0.010 | 0.010 | 0.0050 | 0.0040 |
| Comparative Example 5 | 3,000 | 0.170 | 0.090 | 0.010 | 0.170 | 0.090 | 0.010 | 0.0050 | 0.0040 |
| Comparative Example 6 | 3,000 | 0.170 | 0.060 | 0.030 | 0.170 | 0.060 | 0.030 | 0.0050 | 0.0040 |
| Comparative Example 7 | 3,000 | 0.000 | 0.060 | 0.010 | 0.000 | 0.060 | 0.010 | 0.0050 | 0.0040 |
| Comparative Example 8 | 3,000 | 0.350 | 0.060 | 0.010 | 0.350 | 0.060 | 0.010 | 0.0050 | 0.0040 |

| | Average in entire piezoelectric film | Region in layer form at thickness of 100 nm adjacent to first electrode | | | |
|---|---|---|---|---|---|
| | Bi concentration (mol/mol) | $S_{bou}$ (mol/mol) | Mn concentration (mol/mol) | Bi concentration (mol/mol) | $S_{bou}/S_{ave}$ |
| Example 1 | 0.0010 | 0 | 0 | 0 | 0% |
| Example 2 | 0 | 0 | 0 | 0 | 0% |
| Example 3 | 0.0020 | 0 | 0 | 0 | 0% |
| Example 4 | 0.0050 | 0.0004 | 0.0004 | 0 | 4% |
| Example 5 | 0.0050 | 0.0008 | 0.0008 | 0 | 6% |
| Example 6 | 0.0050 | 0.0015 | 0.0010 | 0.0005 | 10% |
| Example 7 | 0.0010 | 0 | 0 | 0 | 0% |
| Example 8 | 0.0010 | 0 | 0 | 0 | 0% |
| Example 9 | 0.0010 | 0 | 0 | 0 | 0% |
| Example 10 | 0.0010 | 0 | 0 | 0 | 0% |
| Example 11 | 0.0010 | 0 | 0 | 0 | 0% |
| Example 12 | 0.0010 | 0 | 0 | 0 | 0% |
| Example 13 | 0.0010 | 0 | 0 | 0 | 0% |
| Example 14 | 0.0010 | 0 | 0 | 0 | 0% |
| Example 15 | 0.0005 | 0 | 0 | 0 | 0% |
| Example 16 | 0.0010 | 0 | 0 | 0 | 0% |
| Example 17 | 0.0005 | 0.0001 | 0.0001 | 0 | 3% |
| Example 22 | 0.0010 | 0 | 0 | 0 | 0% |
| Example 23 | 0.0010 | 0 | 0 | 0 | 0% |
| Example 24 | 0.0010 | 0 | 0 | 0 | 0% |
| Comparative Example 1 | 0.0010 | 0.0051 | 0.0041 | 0.0010 | 102% |
| Comparative Example 2 | 0 | 0.0021 | 0.0021 | 0 | 11% |
| Comparative Example 3 | 0.0200 | 0.0022 | 0 | 0.0022 | 11% |
| Comparative Example 4 | 0.0010 | 0 | 0 | 0 | 0% |
| Comparative Example 5 | 0.0010 | 0 | 0 | 0 | 0% |
| Comparative Example 6 | 0.0010 | 0 | 0 | 0 | 0% |
| Comparative Example 7 | 0.0010 | 0 | 0 | 0 | 0% |
| Comparative Example 8 | 0.0010 | 0 | 0 | 0 | 0% |

TABLE 4

| | Dielectric loss (25° C.) | Initial constant $d_{31}$ [pm/V] (25° C.) | Constant $d_{31}$ after drive test [pm/V] (25° C.) | Retention rate of constant $d_{31}$ |
|---|---|---|---|---|
| Example 1 | 0.0050 | 95 | 94 | 99% |
| Example 2 | 0.0065 | 89 | 88 | 99% |
| Example 3 | 0.0055 | 91 | 90 | 99% |
| Example 4 | 0.0090 | 94 | 90 | 96% |
| Example 5 | 0.0100 | 95 | 90 | 95% |
| Example 6 | 0.0110 | 98 | 85 | 87% |
| Example 7 | 0.0040 | 87 | 87 | 100% |
| Example 8 | 0.0070 | 119 | 118 | 99% |
| Example 9 | 0.0050 | 86 | 85 | 99% |
| Example 10 | 0.0055 | 109 | 106 | 97% |
| Example 11 | 0.0075 | 104 | 102 | 98% |
| Example 12 | 0.0060 | 97 | 96 | 99% |
| Example 13 | 0.0045 | 90 | 90 | 100% |
| Example 14 | 0.0030 | 77 | 76 | 99% |

TABLE 4-continued

| | Dielectric loss (25° C.) | Initial constant $d_{31}$ [pm/V] (25° C.) | Constant $d_{31}$ after drive test [pm/V] (25° C.) | Retention rate of constant $d_{31}$ |
|---|---|---|---|---|
| Example 15 | 0.0050 | 97 | 93 | 96% |
| Example 16 | 0.0130 | 80 | 75 | 94% |
| Example 17 | 0.0090 | 90 | 86 | 96% |
| Example 22 | 0.0040 | 125 | 125 | 100% |
| Example 23 | 0.0035 | 115 | 115 | 100% |
| Example 24 | 0.0040 | 120 | 120 | 100% |
| Comparative Example 1 | 0.0160 | 105 | 55 | 52% |
| Comparative Example 2 | 0.0185 | 78 | 62 | 79% |
| Comparative Example 3 | 0.0165 | 81 | 61 | 75% |
| Comparative Example 4 | 0.0070 | 59 | Not conducted | Not conducted |
| Comparative Example 5 | 0.0175 | 104 | 79 | 76% |
| Comparative Example 6 | 0.0150 | 108 | 82 | 76% |
| Comparative Example 7 | 0.0150 | 110 | 78 | 71% |
| Comparative Example 8 | 0.0070 | 57 | Not conducted | Not conducted |

EXAMPLE 25

The piezoelectric element according to the second embodiment of the present invention having the configuration illustrated in FIG. 15A was manufactured. Specifically, the piezoelectric element was manufactured in a way similar to that of Example 1 except that the first electrode was not formed and the second electrode was in the shape of combs. The comb electrode pitches were 25 μm, electrode line widths were 10 μm, and a space therebetween was 15 μm.

As a result of composition analysis of the entire piezoelectric film and local composition analysis, $S_{bou}/S_{ave}$ in the vicinity of the comb electrodes was in a range of from 0% to 2%. Further, in the comb electrode portions, only Pt and Ti were detected and Mn and Bi were not detected, and it was found that the total content of Mn and Bi in the electrode portions was less than 50 ppm.

Further, as illustrated in FIG. 15B, an external power supply was connected to the comb electrodes opposed to each other to form the surface acoustic wave generator according to the present invention. Excitation of a surface acoustic wave in response to an input alternating voltage was confirmed, and, even when the surface acoustic wave generator was continuously driven $10^{10}$ times or more, a surface acoustic wave similar to the initial one was excited.

(Influence of Manufacturing Method)

In Examples 1 to 25, the piezoelectric film was manufactured by CSD, but an equivalent piezoelectric element can be manufactured by MOCVD using the first raw material liquid, the second raw material liquid, and the third raw material liquid or RF sputtering using targets having different compositions instead of the first raw material liquid, the second raw material liquid, and the third raw material liquid, and the effects of the present invention can be obtained.

(Influence of Mn Amount and Bi Amount)

When the Mn content was more than 0.004 moles for 1 mole of the metal oxide as the principal component, piezoelectric properties similar to those of Example 1 were able to be obtained when the Mn content was up to 0.008 moles. The piezoelectric properties include the retention rate of the piezoelectric constant when the piezoelectric element was continuously driven, which was 95% or more. However, when the Mn amount was 0.02 moles, the dielectric loss at room temperature was more than 1.8%

On the other hand, when the Mn content was smaller than 0.004 moles, piezoelectric properties similar to those of Example 1 were able to be obtained when the Mn content was down to 0.002 moles. However, when no Mn was added or no Bi was added, the piezoelectric constant was steeply reduced (by more than 20%) and the dielectric loss was steeply increased (by more than 30%). Further, the retention rate of the piezoelectric constant when the piezoelectric element was continuously driven was less than 70%.

When, under the existence of Mn, the Bi content was more than 0.001 moles for 1 mole of the metal oxide as the principal component, piezoelectric properties similar to those of Example 1 were able to be obtained when the Bi content was up to 0.005 moles. However, when the Bi content was 0.02 moles, the dielectric loss at room temperature was more than 1.6%.

(Influence of Zr Amount, Sn Amount, and Ti Amount)

When y representing the mole ratio of Zr was increased from 0.06 to 0.085, as the amount increased, the initial piezoelectric constant of the continuous drive test and the piezoelectric constant after the drive test increased by about 25% at the maximum, but the retention rate of the piezoelectric constant in the continuous drive test was not influenced. However, when y=0.090, under the influence of the lowered Curie temperature, the dielectric loss measured at 50° C. was more than 1.5%, and at the same time, the retention rate of the piezoelectric constant in the continuous drive test was less than 80%.

On the other hand, when y representing the mole ratio of Zr was reduced from 0.06, the piezoelectric constants were reduced at the respective temperatures by less than 10% down to y=0.025. However, when y=0.010, the piezoelectric constant was reduced by more than 25%.

When z representing the mole ratio of Sn was changed from 0.01 to 0.02, the initial piezoelectric constant of the continuous drive test and the piezoelectric constant after the drive test increased by about 15%, but the retention rate of the piezoelectric constant in the continuous drive test was not influenced. However, when z was changed to 0.03 under a condition in which y was 0.06 or more, under the influence of the lowered Curie temperature, the dielectric loss measured at 50° C. was more than 1.5%, and at the same time, the retention rate of the piezoelectric constant in the continuous drive test was less than 80%.

On the other hand, when z was changed to zero, the initial piezoelectric constant of the continuous drive test and the piezoelectric constant after the drive test reduced by about 10%, but the retention rate of the piezoelectric constant in the continuous drive test was not influenced.

(Influence of Ca Amount and Ba Amount)

When x representing the mole ratio of Ca was increased from 0.17 to 0.20, as the amount increased, the initial piezoelectric constant of the continuous drive test and the piezoelectric constant after the drive test decreased by about 5% at the maximum, but the retention rate of the piezoelectric constant in the continuous drive test was not influenced.

When x representing the mole ratio of Ca was increased from 0.17 to 0.30, as the amount increased, the initial piezoelectric constant of the continuous drive test and the piezoelectric constant after the drive test decreased by about 20% at the maximum, but the retention rate of the piezoelectric constant in the continuous drive test was not influenced. However, when x=0.35, the piezoelectric constant reduced by more than 25%.

On the other hand, when x was reduced from 0.17 to 0.09, as the amount reduced, the initial piezoelectric constant of the continuous drive test and the piezoelectric constant after the drive test increased by about 10% at the maximum, but the retention rate of the piezoelectric constant in the continuous drive test was not influenced. However, when Ca substitution was zero, under the influence of the raised $T_{ro}$ to the vicinity of room temperature, change in piezoelectric constant with respect to temperature was increased. Further, the retention rate of the piezoelectric constant in the continuous drive test was less than 80%.

(Piezoelectric Actuator)

The piezoelectric element of Example 1 was used to manufacture the piezoelectric actuator having the structure illustrated in FIG. 3A and FIG. 3B. Displacement of a thin piece portion of the piezoelectric actuator depending on application of an alternating voltage was confirmed. Note that, as the diaphragm, a $SiO_2$ film having a thickness of 5 μm was used. The amount of displacement of the thin piece portion of the piezoelectric actuator using the piezoelectric element of Example 1 was more than twice as much as that using the piezoelectric element of Comparative Example.

(Liquid Ejection Head)

A liquid ejection head having the structure illustrated in FIG. 4A was manufactured using the piezoelectric element of Example 1.

Liquid droplet ejection performance of the obtained liquid ejection head when the applied voltage was 20 V at 10 kHz was evaluated. The ejection performance of the liquid ejection head of Example was satisfactory.

(Liquid Ejection Apparatus)

The liquid ejection head described above was used to manufacture the liquid ejection apparatus illustrated in FIG. 4B. Ink ejection in response to an input electrical signal was confirmed.

(Vibration Correction Mechanism)

The piezoelectric actuator described above was used to manufacture the vibration correction mechanism illustrated in FIG. 5. As the transfer target, a glass lens and a CMOS element were used. Rotational movement of the transfer target in response to an input electrical signal was confirmed.

(Variable Optical Member)

The piezoelectric actuator described above was used to manufacture the variable optical member illustrated in FIG. 6A. As the optical member, a polyacrylic acid-based plastic lens was used. Deformation of the optical member in response to an input electrical signal was confirmed.

(Movable Optical Member)

The piezoelectric actuator described above was used to manufacture the movable optical member illustrated in FIG. 6B. As the piezoelectric strain transfer unit, a metal rod made of aluminum was used, and, as the optical member, a mirror formed by evaporating aluminum on a glass plate was used. Movement or rotation of the optical member in response to an input electrical signal was confirmed.

(Optical Device)

The vibration correction mechanism described above was used to manufacture the optical device illustrated in FIG. 7A. It was confirmed that change in optical path of exiting light due to a vibration from the outside was able to be suppressed by the function of the vibration correction mechanism. Further, the variable optical member described above or the movable optical member described above was used to manufacture the optical devices illustrated in FIG. 7B and FIG. 7C. Change in optical path in response to application of an alternating voltage was confirmed.

(Image Pickup Apparatus)

The vibration correction mechanism described above was used to manufacture the image pickup apparatus illustrated in FIG. 8. It was confirmed that change in a taken image due to a vibration from the outside was able to be suppressed by the function of the vibration correction mechanism.

(Optical Switch)

The variable optical member in which the piezoelectric actuator described above and an optical fiber are dynamically connected was used to manufacture the optical switch illustrated in FIG. 9A. Switching operation of the optical switch in response to an input electrical signal was confirmed. Further, the piezoelectric actuator described above and the element illustrated in FIG. 9B were dynamically connected to manufacture the optical switch. Switching operation of the optical switch in response to an input electrical signal was confirmed.

(Micromirror Device)

The piezoelectric actuator described above was used to manufacture the micromirror device illustrated in FIG. 10. As the piezoelectric strain transfer unit, a metal rod made of aluminum was used. Movement and rotation of the micromirror device in response to an input electrical signal was confirmed.

(Ultrasonic Wave Probe)

The piezoelectric actuator described above was used to manufacture the ultrasonic wave probe illustrated in FIG. 11A. Operation of sending an ultrasonic wave in response to an input electrical signal and operation of receiving an ultrasonic wave reflected by a subject were confirmed.

(Ultrasonograph)

The ultrasonic wave probe described above was used to manufacture the ultrasonograph illustrated in FIG. 11B. Generation of an ultrasonic wave image with reduced noise from oscillation data of an output/input ultrasonic wave was confirmed.

(Sound Component)

The piezoelectric actuator described above was used to manufacture the sound component illustrated in FIG. 12. Sending of a sound wave in response to an input electrical signal or receiving of a sound wave from the outside was confirmed.

(Angular Velocity Sensor)

The piezoelectric element of Example 1 was used to manufacture the angular velocity sensor having the signal processing unit illustrated in FIG. 13. It was confirmed that change in shape due to movement, rotation, or the like of the sensor body was converted into angular velocity information by the processing unit.

(Vibration Power Generator)

The piezoelectric element of Example 1 was used to manufacture the vibration power generator illustrated in FIG. 14. The vibration power generator was placed on a mechanical pump, and the mechanical pump was actuated. It was confirmed that power generating operation in which vibrational energy was converted into electric energy was performed.

(Piezoelectric Shutter)

The surface acoustic wave generator of Example 2 was used to manufacture the piezoelectric shutter illustrated in FIG. 15C. The piezoelectric film and the comb electrodes were formed on both surfaces of the substrate. Opening/closing operation of the piezoelectric shutter in response to an input electrical signal was confirmed.

The piezoelectric element according to the present invention has a piezoelectric constant that does not change much while the piezoelectric element is continuously driven. Further, the piezoelectric element does not contain lead, and thus, loads on the environment are light. Therefore, the piezoelectric element according to the present invention is applicable to a piezoelectric actuator, a liquid ejection head, a liquid ejection apparatus, a vibration correction mechanism, a variable optical member, a movable optical member, an optical device, an image pickup apparatus, an optical switch, a micromirror device, an ultrasonic wave probe, an ultrasonograph, a sound component, an angular velocity sensor, a vibration power generator, a surface acoustic wave generator, a piezoelectric shutter, and other piezoelectric apparatus as a whole that use the piezoelectric function.

According to the present invention, a thin film type piezoelectric element having a piezoelectric constant that does not change much while the piezoelectric element is continuously driven, and a manufacturing method therefor can be provided.

Further, according to the present invention, there can be provided a piezoelectric actuator, a liquid ejection head, a liquid ejection apparatus, a vibration correction mechanism, a variable optical member, a movable optical member, an optical device, an image pickup apparatus, an optical switch, a micromirror device, an ultrasonic wave probe, an ultrasonograph, a sound component, an angular velocity sensor, a vibration power generator, a surface acoustic wave generator, a piezoelectric shutter, and an electronic apparatus that use the piezoelectric element.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-231845, filed Nov. 27, 2015, which is hereby incorporated by reference herein in its entirety.

What is claimed is:

1. A piezoelectric element comprising:
a substrate;
electrodes; and
a piezoelectric film,
wherein the piezoelectric film comprises an oxide including Ba, Ca, Ti, and Zr, and at least one element of Mn and Bi,
wherein $0.09 \leq x \leq 0.30$, where x is a mole ratio of Ca to a sum of Ba and Ca,
wherein $0.025 \leq y \leq 0.085$, where y is a mole ratio of Zr to a sum of Ti, Zr, and Sn,
wherein $0 \leq z \leq 0.02$, where z is a mole ratio of Sn to the sum of Ti, Zr, and Sn,
wherein a total content $S_{ave}$ of the at least one element of Mn and Bi is 0.0020 moles to 0.0150 moles for 1 mole of the oxide, and
wherein a total content $S_{bou}$ of the at least one element of Mn and Bi in a region of the piezoelectric film adjacent to one of the electrodes is smaller than $S_{ave}$.

2. The piezoelectric element according to claim 1, wherein the piezoelectric film comprises a perovskite-type metal oxide expressed by general formula (1):

$$(Ba_{1-x}Ca_x)(Ti_{1-y-z}Zr_ySn_z)O_3 \quad (1),$$

provided that $0.09 \leq x \leq 0.30$, $0.025 \leq y \leq 0.085$, and $0 \leq z \leq 0.02$.

3. The piezoelectric element according to claim 1, wherein the electrodes comprise any one of Au, Ag, Pd, Pt, Ni, and Ru.

4. The piezoelectric element according to claim 1, wherein the total content $S_{bou}$ of the at least one element of Mn and Bi in a region that is 5% or less of a thickness of the piezoelectric film is smaller than $S_{ave}$.

5. The piezoelectric element according to claim 1, wherein $S_{bou}$ and $S_{ave}$ are such that $0\% \leq S_{bou}/S_{ave} \leq 10\%$.

6. The piezoelectric element according to claim 1, wherein, in the region of the piezoelectric film adjacent to the one of the electrodes, $|x-x'| \leq 0.02$, $|y-y'| \leq 0.01$, and $|z-z'| \leq 0.01$ when a local composition of Ba, Ca, Ti, Zr, and Sn is expressed by general formula (2):

$$(Ba_{1-x'}Ca_{x'})(Ti_{1-y'-z'}Zr_{y'}Sn_{z'})O_3 \quad (2).$$

7. The piezoelectric element according to claim 1, further comprising an adhesion component comprising a metal of Group 4 elements and/or Group 5 elements, and existing between the one of the electrodes and the substrate.

8. The piezoelectric element according to claim 1, wherein the piezoelectric film has an aggregate structure comprising a grain having a columnar structure.

9. A piezoelectric actuator comprising:
the piezoelectric element of claim 1; and
a diaphragm provided to the piezoelectric element.

10. A vibration correction mechanism comprising two or more piezoelectric actuators of claim 9,
wherein the two or more piezoelectric actuators are arranged such that, when a voltage is applied thereto, the two or more piezoelectric actuators expand and contract in two or more directions.

11. An optical device comprising:
the vibration correction mechanism of claim 10; and
an optical member held by the vibration correction mechanism.

12. An image pickup apparatus comprising:
the vibration correction mechanism of claim 10; and
an image pickup element unit held by the vibration correction mechanism.

13. A variable optical member comprising:
the piezoelectric actuator of claim 9;
an optical member dynamically connected to the piezoelectric actuator; and
a mechanism for changing a shape of the optical member through deformation of the piezoelectric actuator.

14. An optical device comprising the variable optical member of claim 13.

15. An optical switch comprising the variable optical member of claim 13.

16. A sound component comprising the piezoelectric actuator of claim 15 and being configured to perform one of sending and receiving sound through driving of the piezoelectric actuator.

17. A movable optical member comprising:
the piezoelectric actuator of claim 9;
an optical member dynamically connected to the piezoelectric actuator; and
a mechanism for moving and/or rotating the optical member through deformation of the piezoelectric actuator.

18. An optical device comprising the movable optical member of claim 17.

19. An optical switch comprising the movable optical member of claim 17.

20. A micromirror device comprising:
a plurality of micromirrors; and
a plurality of piezoelectric actuators dynamically connected to the plurality of micromirrors, respectively,
wherein each of the plurality of piezoelectric actuators is the piezoelectric actuator of claim 9.

21. An ultrasonic wave probe comprising the piezoelectric actuator of claim 9, the ultrasonic wave probe having a function of oscillating an ultrasonic wave and a function of receiving a reflected wave.

22. An ultrasonograph comprising:
the ultrasonic wave probe of claim 21;
a signal processing unit; and
an image generating unit.

23. A liquid ejection head comprising:
a liquid chamber comprising a vibration portion comprising the piezoelectric element of claim 1; and
an ejection orifice communicating with the liquid chamber.

24. A liquid ejection apparatus comprising:
a placing portion for a transfer target; and
the liquid ejection head of claim 23.

25. An angular velocity sensor comprising the piezoelectric element of claim 1 and being configured to convert change in shape of the piezoelectric element into angular velocity information.

26. A vibration power generator comprising the piezoelectric element of claim 1 and being configured to convert vibrational energy into electric energy.

27. An electronic apparatus comprising:
an electronic component; and
the piezoelectric element of claim 1, the piezoelectric element being provided to the member.

28. A piezoelectric element comprising:
a substrate;
a piezoelectric film; and
a plurality of comb electrodes,
wherein the piezoelectric film comprises an oxide including Ba, Ca, Ti, and Zr, and at least one element of Mn and Bi,
wherein $0.09 \leq x \leq 0.30$, where x is a mole ratio of Ca to a sum of Ba and Ca,
wherein $0.025 \leq y \leq 0.085$, where y is a mole ratio of Zr to a sum of Ti, Zr, and Sn,
wherein $0 \leq z \leq 0.02$, where z is a mole ratio of Sn to the sum of Ti, Zr, and Sn,
wherein a total content $S_{ave}$ of the at least one element of Mn and Bi is 0.0020 moles to 0.0150 moles for 1 mole of the oxide, and
wherein a total content $S_{bou}$ of the at least one element of Mn and Bi in a region of the piezoelectric film adjacent to one of the plurality of comb electrodes is smaller than $S_{ave}$.

29. The piezoelectric element according to claim 28, wherein the piezoelectric film comprises a perovskite-type metal oxide expressed by general formula (1):

$$(Ba_{1-x}Ca_x)(Ti_{1-y-z}Zr_ySn_z)O_3 \qquad (1),$$

provided that $0.09 \leq x \leq 0.30$, $0.025 \leq y \leq 0.085$, and $0 \leq z \leq 0.02$.

30. A surface acoustic wave generator, comprising the piezoelectric element of claim 28.

31. A piezoelectric shutter, comprising:
the surface acoustic wave generator of claim 30; and
a light-shielding component configured to move through driving of the surface acoustic wave generator.

32. An electronic apparatus comprising:
an electronic component; and
the piezoelectric element of claim 28, the piezoelectric element being provided to the member.

33. A method of manufacturing a piezoelectric element, comprising:
(a) applying a first raw material liquid onto a substrate having a first electrode layer formed on a surface thereof to form an applied layer;
(b) firing the applied layer every time the applied layer is formed to form a piezoelectric body layer, the steps (a) and (b) being conducted once or a plurality of times to form a piezoelectric film lower layer;
(c) applying a second raw material liquid onto the piezoelectric film lower layer to form a first applied layer;
(d) firing the first applied layer every time the first applied layer is formed to form a piezoelectric body layer, the steps (c) and (d) being conducted once or a plurality of times to form a piezoelectric film intermediate layer;
(e) applying a third raw material liquid onto the piezoelectric film intermediate layer to form a second applied layer;
(f) firing the second applied layer every time the second applied layer is formed to form a piezoelectric body layer, the steps (e) and (f) being conducted once or a plurality of times to form a piezoelectric film upper layer; and
(g) forming a second electrode layer on a surface of the piezoelectric film upper layer to manufacture the piezoelectric element,
wherein the second raw material liquid comprises Ba, Ca, Ti, and Zr, and comprises at least one of Mn and Bi, and
wherein the first raw material liquid and the third raw material liquid comprise Ba, Ca, Ti, and Zr, with a concentration of a sum of Mn and Bi in the first raw material liquid and the third raw material liquid being 1,000 ppm or less.

* * * * *